(12) United States Patent
Abbott et al.

(10) Patent No.: US 9,372,142 B2
(45) Date of Patent: Jun. 21, 2016

(54) LIQUID CRYSTAL DEVICE AND METHOD FOR SCREENING PROTEIN STABILIZING AGENTS OR OPTIMAL PROTEIN CONCENTRATIONS TO PREVENT UNFOLDING

(71) Applicant: Wisconsin Alumni Research Foundation, Madison, WI (US)

(72) Inventors: Nicholas L. Abbott, Madison, WI (US); Lie Na Tan, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 289 days.

(21) Appl. No.: 13/778,564

(22) Filed: Feb. 27, 2013

(65) Prior Publication Data

US 2013/0224780 A1    Aug. 29, 2013

Related U.S. Application Data

(60) Provisional application No. 61/603,435, filed on Feb. 27, 2012.

(51) Int. Cl.
*G01N 13/00* (2006.01)
*G01N 13/02* (2006.01)
(Continued)

(52) U.S. Cl.
CPC .............. *G01N 13/00* (2013.01); *C09K 19/062* (2013.01); *C09K 19/2014* (2013.01);
(Continued)

(58) Field of Classification Search
CPC .................................................. G01N 13/00
USPC .................. 422/82.05, 82.09; 435/23, 287.1; 436/4–5
See application file for complete search history.

(56) References Cited

U.S. PATENT DOCUMENTS 4,642,294 A * 2/1987 Arnaud et al. ..................... 436/5
4,771,004 A * 9/1988 Higuchi ............................ 436/5
(Continued)

FOREIGN PATENT DOCUMENTS

WO    WO 90/14591    * 11/1990

OTHER PUBLICATIONS

Alino, et al., Liquid Crystal Droplets as a Hosting and Sensing Platform for Developing Immunoassays, Langmuir, 2011, 27(19):11784-11789.
(Continued)

*Primary Examiner* — Arlen Soderquist
(74) *Attorney, Agent, or Firm* — Boyle Fredrickson S.C.

(57) ABSTRACT

Methods and devices for assaying the effectiveness of a cleaning composition in removing a protein or a biofilm from a surface are disclosed. Such methods include the steps of providing one or more proteins at an interface between an aqueous phase and a liquid crystal phase or at the surface of a liquid crystal, contacting the interface or liquid crystal surface with a cleaning composition, and observing the orientational ordering of the liquid crystal at the interface or liquid crystal surface. A continuous change in the orientational ordering of the liquid crystal at the interface or liquid crystal surface indicates that the proteins are being removed from the interface, and the rate of change in orientational ordering, the extent of the change in orientational ordering, or both, are correlated with the effectiveness of the cleaning composition. Because the ability of cleaning agents to remove proteins from the interface or liquid crystal surface is correlated with the state and concentration of the protein that is being removed, similar methods and devices can be used to assay the effectiveness of a putative protein stabilizing agent or to assay the optimal concentration of a protein for preventing the unfolding of the protein.

18 Claims, 13 Drawing Sheets

(51) Int. Cl.

| | |
|---|---|
| *G01N 21/77* | (2006.01) |
| *C09K 19/06* | (2006.01) |
| *C09K 19/20* | (2006.01) |
| *C09K 19/22* | (2006.01) |
| *C09K 19/24* | (2006.01) |
| *C09K 19/26* | (2006.01) |
| *C09K 19/28* | (2006.01) |
| *C09K 19/34* | (2006.01) |
| *A61L 2/28* | (2006.01) |
| *G01N 21/23* | (2006.01) |
| *C09K 19/12* | (2006.01) |
| *C09K 19/30* | (2006.01) |

(52) U.S. Cl.
CPC ............... *C09K 19/22* (2013.01); *C09K 19/24* (2013.01); *C09K 19/26* (2013.01); *C09K 19/28* (2013.01); *C09K 19/3458* (2013.01); *G01N 13/02* (2013.01); *G01N 21/77* (2013.01); *A61L 2/28* (2013.01); *C09K 2019/122* (2013.01); *C09K 2019/2042* (2013.01); *C09K 2019/2078* (2013.01); *C09K 2019/3083* (2013.01); *C09K 2219/17* (2013.01); *G01N 21/23* (2013.01); *G01N 2013/0275* (2013.01)

(56) References Cited

U.S. PATENT DOCUMENTS

| | | | | |
|---|---|---|---|---|
| 4,976,861 | A * | 12/1990 | Pall | 210/508 |
| 4,988,625 | A * | 1/1991 | Marburg et al. | 436/5 |
| 5,053,340 | A * | 10/1991 | Bergman et al. | 436/5 |
| 5,155,555 | A * | 10/1992 | Wetegrove et al. | 356/632 |
| 5,268,306 | A * | 12/1993 | Berger et al. | 436/527 |
| 5,411,888 | A * | 5/1995 | Gordon et al. | 436/5 |
| 6,085,153 | A * | 7/2000 | Hirsh et al. | 702/22 |
| 6,096,550 | A * | 8/2000 | Argo | 436/5 |
| 6,272,436 | B1 * | 8/2001 | Hirsh et al. | 702/27 |
| 6,284,197 | B1 * | 9/2001 | Abbott et al. | 422/82.05 |
| 6,797,463 | B2 * | 9/2004 | Abbott et al. | 435/5 |
| 6,849,321 | B2 * | 2/2005 | Abbott et al. | 428/141 |
| 7,125,592 | B2 * | 10/2006 | Abbott et al. | 428/1.5 |
| 7,459,124 | B2 * | 12/2008 | Abbott et al. | 422/412 |
| 7,666,661 | B2 * | 2/2010 | Abbott et al. | 435/287.1 |
| 7,678,545 | B2 * | 3/2010 | Abbott et al. | 435/7.1 |
| 7,732,152 | B2 * | 6/2010 | Abbott et al. | 435/7.21 |
| 7,745,220 | B2 * | 6/2010 | Abbott et al. | 436/4 |
| 7,795,007 | B2 * | 9/2010 | Abbott et al. | 435/287.2 |
| 7,910,382 | B2 * | 3/2011 | Abbott et al. | 436/518 |
| 7,947,510 | B2 * | 5/2011 | Schwartz et al. | 436/164 |
| 8,125,640 | B2 * | 2/2012 | Abbott et al. | 356/364 |
| 8,133,680 | B2 * | 3/2012 | Abbott et al. | 435/7.1 |
| 8,633,034 | B2 * | 1/2014 | Trotter et al. | 436/546 |
| 2003/0194753 | A1 * | 10/2003 | Abbott et al. | 435/7.9 |
| 2004/0038408 | A1 * | 2/2004 | Abbott et al. | 436/4 |
| 2004/0091620 | A1 * | 5/2004 | Abbott et al. | 427/250 |
| 2005/0037501 | A1 * | 2/2005 | Meyer et al. | 436/5 |
| 2005/0064395 | A1 * | 3/2005 | Israel et al. | 435/5 |
| 2005/0106562 | A1 * | 5/2005 | Abbott et al. | 435/5 |
| 2006/0003389 | A1 * | 1/2006 | Abbott et al. | 435/7.9 |
| 2007/0042505 | A1 * | 2/2007 | Israel et al. | 436/518 |
| 2007/0099249 | A1 * | 5/2007 | Abbott et al. | 435/7.5 |
| 2007/0231832 | A1 * | 10/2007 | Abbott et al. | 435/7.4 |
| 2007/0269630 | A1 * | 11/2007 | Abbott et al. | 435/30 |
| 2008/0034848 | A1 * | 2/2008 | Cloete et al. | 73/61.48 |
| 2009/0061527 | A1 * | 3/2009 | Schwartz et al. | 436/94 |
| 2009/0262350 | A1 * | 10/2009 | Abbott et al. | 356/365 |
| 2010/0009344 | A1 * | 1/2010 | Israel et al. | 435/5 |
| 2010/0081123 | A1 * | 4/2010 | Abbott et al. | 435/5 |
| 2010/0093096 | A1 * | 4/2010 | Acharya et al. | 436/4 |
| 2010/0221815 | A1 * | 9/2010 | Abbott et al. | 435/287.1 |
| 2011/0141431 | A1 * | 6/2011 | Jordan | 349/199 |
| 2012/0135450 | A1 * | 5/2012 | Abbott et al. | 435/29 |
| 2013/0224780 | A1 * | 8/2013 | Abbott et al. | 435/23 |

OTHER PUBLICATIONS

Berquand, et al., Two-Step Formation of Streptavidin-Supported Lipid Bilayers by PEG-Triggered Vesicle Fusion. Fluorescence and Atomic Force Microscopy Characterization, Langmuir, 2003, 19:1700-1707.

Brake, et al., An Experimental System for Imaging the Reversible Adsorption of Amphiphiles at Aqueous-Liquid Crystal Interfaces, Langmuir, 2002, 18(16):6101-6109.

Brake, et al., Biomolecular Interactions at Phospholipid-Decorated Surfaces of Liquid Crystals, Science, 2003, 302:2094-2097.

Brake, et al., Effect of Surfactant Structure on the Orientation of Liquid Crystals at Aqueous-Liquid Crystal Interfaces, Langmuir, 2003, 19(16):6436-6442.

Brake, et al., Formation and Characterization of Phospholipid Monolayers Spontaneously Assembled at Interfaces Between Aqueous Phases and Thermotropic Liquid Crystals, Langmuir, 2005, 21:2218-2228.

Brake, et al., Coupling of the Orientations of Thermotropic Liquid Crystals to Protein Binding Events at Lipid-Decorated Interfaces, Langmuir, 2007, 23:8497-8507.

Fletcher, et al., UV Polymerisation of Surfactants Adsorbed at the Nematic Liquid Crystal—Water Interface Produces an Optical Response, ChemPhysChem, 2009, 10(17):3046-3053.

Gupta, et al., Elastic Energy-Driven Phase Separation of Phospholipid Monolayers at the Nematic Liquid-Crystal—Aqueous Interface, Physical Review Letters, 2008, 100:048301, 4 pages.

Gupta, et al., Principles for Manipulation of the Lateral Organization of Aqueous-Soluble Surface-Active Molecules at the Liquid Crytal-Aqueous Interface, Langmuir, 2009, 25(4):2026-2033.

Jang, et al., Using Liquid Crystals to Report Membrane Proteins Captured by Affinity Microcontact Printing from Cell Lysates and Membrane Extracts, J. Am. Chem. Soc., 2005, 127:8912-8913.

Kinsinger, et al., Reversible Control of Ordering Transitions at Aqueous/Liquid Crystal Interfaces Using Functional Amphiphilic Polymers, Advanced Materials, 2007, 19(23):4208-4212.

Kinsinger, et al., Nematic Ordering Drives the Phase Separation of Mixed Monolayers Containing Phospholipids Modified with Poly-(ethylene glycol) at Aqueous-Liquid Crystal Interfaces, Soft Matter, 2010, 6:4095-4104.

Kwok, et al., Nano-Structured Alignment Layers for Liquid Crystal Displays, Molecular Crystals and Liquid Crystals, 2009, 507(1):26-40.

Lee, et al., pH-responsive Aqueous/LC Interfaces Using SGLCP-b-polyacrylic Acid Block Copolymers, Soft Matter, 2010, 6:1964-1970.

Lockwood, et al., Influence of Surfactant Tail Branching and Organization on the Orientation of Liquid Crystals at Aqueous-Liquid Crystal Interfaces, Langmuir, 2005, 21(15):6805-6814.

Lockwood, et al., Self-Assembly of Surfactants and Phospholipids at Interfaces Between Aqueous Phases and Thermotropic Liquid Crystals, Current Opinion in Colloid & Interface Science, 2005, 10(3-4):111-120.

Lockwood, et al., Thermotropic Liquid Crystals as Substrates for Imaging the Reorganization of Matrigel by Human Embryonic Stem Cells, Advanced Functional Materials, 2006, 16(5):618-624.

Lockwood, et al., Self-Assembly of Amphiphiles, Polymers and Proteins at Interfaces Between Thermotropic Liquid Crystals and Aqueous Phases, Surface Science Reports, 2008, 63:255-293.

Luk, et al., Using Liquid Crystals to Amplify Protein-Receptor Interactions: Design of Surfaces with Nanometer-Scale Topography that Present Histidine-Tagged Protein Receptors, Langmuir, 2003, 19(5):1671-1680.

Meli, et al., Preparation of Microscopic and Planar Oil-Water Interfaces That Are Decorated with Prescribed Densities of Insoluble Amphiphiles, J. Am. Chem. Soc., 2008, 130(13):4326-4333.

Park, et al., Ordering Transitions in Thermotropic Liquid Crystals Induced by the Interfacial Assembly and Enzymatic Processing of Oligopeptide Amphiphiles, Advanced Materials, 2008, 20(6):1185-1190.

(56) References Cited

OTHER PUBLICATIONS

Pignataro, et al., Specific Adhesion of Vesicles Monitored by Scanning Force Microscopy and Quartz Crystal Microbalance, Biophysical Journal, 2000, 78:487-498.

Price, et al., DNA Hybridization-Induced Reorientation of Liquid Crystal Anchoring at the Nematic Liquid Crystal/Aqueous Interface, J. Am. Chem. Soc., 2008, 130:8188-8194.

Stadler, et al., Micropatterning of DNA-Tagged Vesicles, Langmuir, 2004, 20(26):11348-11354.

Stora, et al., Histidine-Tagged Amphiphiles for the Reversible Formation of Lipid Bilayer Aggregates on Chelator-Functionalized Gold Surfaces, Langmuir, 2000, 16(12):5471-5478.

Tan, et al., Ordering Transitions in Nematic Liquid Crystals Induced by Vesicles Captured Through Ligand-Receptor Interactions, Langmuir, 2011, 27(4):1419-1429.

Tingey, et al., Imaging of Affinity Microcontact Printed Proteins by Using Liquid Crystals, Langmuir, 2004, 20:6818-6826.

* cited by examiner

LIQUID CRYSTAL DEVICE AND METHOD FOR SCREENING PROTEIN STABILIZING AGENTS OR OPTIMAL PROTEIN CONCENTRATIONS TO PREVENT UNFOLDING

CROSS REFERENCE TO RELATED APPLICATIONS

This application claims the benefit of U.S. Provisional Application No. 61/603,435 filed on Feb. 27, 2012, which is incorporated by reference herein in its entirety.

STATEMENT REGARDING FEDERALLY SPONSORED RESEARCH OR DEVELOPMENT

This invention was made with government support under 0520527 awarded by the National Science Foundation and CA108467 awarded by the National Institutes of Health. The government has certain rights in the invention.

FIELD OF THE INVENTION

The invention relates generally to methods and devices for assaying the effectiveness of cleaning compositions. More particularly, the invention relates to methods and devices for assessing the ability of a cleaning composition to remove proteins or biofilms from a surface. The invention can also be used to test of the stability of proteins at interfaces and in bulk solution, and to screen for putative agents that promote the stabilization of the folding of the proteins both at interfaces and in bulk solution. Finally, embodiments of the invention can be used to identify agents that prevent the adsorption of proteins and biofilms to surfaces.

BACKGROUND OF THE INVENTION

Proteins, polysaccharides, biofilms, and other contaminants may collect on surfaces over time in a process known as surface fouling. The identification of agents that prevent the adsorption of biofouling agents to surfaces is technologically important in contexts such as water purification, membrane separations processes, design of surfaces of biomedical devices and storage of therapeutic proteins. Surface-contaminating agents may be removed from fouled surfaces using a variety of cleaning formulations, typically including detergents, polymers, lipids, enzymes, or mixtures thereof. The identification and optimization of effective cleaning formulations has led to the development of a range of consumer products for home use and commercial products used in the food, drug, paper, and medical industries. Because of ever increasing material costs and growing environmental concerns, there is a continuing need for improved methods for efficiently identifying cleaning formulations for removing contaminating agents from surfaces and for optimizing the concentrations of the active ingredients contained in such formulations. In addition, identification of agents that prevent biofouling is an important goal of many investigators.

Proteins are often unstable when not in their native environments. For example, over time, proteins may unfold or flatten, may become cross-linked, or the primary structure of the proteins may break down. Yet purified proteins, such as those used in protein-based therapeutics and in other pharmaceuticals, often need to be stored for an extended period of time while retaining their original structural integrity and conformation. Stabilizing agents can be used to slow the degradation process; however, such agents have exhibited inconsistent results with different proteins and under different conditions, and maintaining the stability of purified proteins remains a major problem in the pharmaceutical and health care industries. Accordingly, there is a continuing need for improved methods for efficiently identifying agents for effectively stabilizing proteins and other biomolecules.

SUMMARY OF THE INVENTION

The inventors have developed a model liquid crystal-based system for studying the behavior and conformation of proteins at a surface or other interface. The model system includes one or more protein molecules disposed at a liquid crystal-aqueous interface. As proteins are removed from the interface, the liquid crystal surprisingly undergoes a continuous orientational ordering transition. This ordering transition, which is correlated to the extent and speed of protein removal from the interface, can be readily measured. Accordingly, the inventors' model system can be used to rapidly assay the effectiveness of a given cleaning composition in removing proteins or biofilms from a surface or other interface. In addition, the inventors' model can be used to rapidly assay the effectives of agents for prevention of adsorption of proteins and other naturally occurring molecules to surfaces.

Furthermore, the inventors have determined that in the model system, proteins that have aged (i.e., unfolded and/or cross-linked) are more difficult to remove from the interface, and that proteins that are crowded at the interface (i.e., less likely to be unfolded) are easier to remove from the interface. Accordingly, the inventors' model system can be used to rapidly assay the state or conformation of proteins. Such an assay could be used, for example, to evaluate the effectiveness of potential protein stabilizing agents.

In a first aspect, the disclosure encompasses a method for assaying the effectiveness of a cleaning composition in removing a protein or a biofilm from a surface. The method includes the steps of (a) providing one or more proteins at an interface between an aqueous phase and a liquid crystal phase; (b) contacting the interface with a cleaning composition; and (c) observing the orientational ordering of the liquid crystal at the interface. In the method, a continuous change in the orientational ordering of the liquid crystal at the interface indicates that the proteins are being removed from the interface, and the rate of the change in orientational ordering, the extent of the change in orientational ordering, or both, are correlated with the effectiveness of the cleaning composition in removing a protein or a biofilm from a surface.

In some embodiments, the liquid crystal phase comprises a low molecular weight liquid crystal, a liquid crystal elastomer, a liquid crystalline gel, or a liquid crystal droplet. In certain such embodiments, the low molecular weight liquid crystal is nematic 4'-pentyl-4-cyanobiphenyl (5CB).

In some embodiments, the cleaning composition includes a detergent, a polymer, a surfactant, a lipid, an enzyme, or a mixture thereof. In certain such embodiments, the enzyme is a protease.

In some embodiments, the one or more proteins provided at the interface are selected from streptavidin, conjugated streptavidin, and anti-biotin antibody.

In some embodiments, the step of observing the orientational ordering of the liquid crystal at the interface is performed by detecting polarized light that is passed through the interface. Optionally, the polarized light is passed through the interface between crossed polarizers.

In some embodiments, the step of observing the orientational ordering of the liquid crystal at the interface includes the step of calculating the tilt angle of the liquid crystal at the interface relative to the interface normal, wherein the tilt angle indicates the extent of the change in orientational ordering. Optionally, the tilt angle is calculated from the effective birefringence of the liquid crystal under light illumination.

In a second aspect, the disclosure encompasses a method for validating a cleaning process. The method includes the steps of (a) contacting a cleaning solution with a surface to be cleaned; (b) adding a liquid crystal having one or more proteins adsorbed to the liquid crystal surface to the cleaning solution; and (c) observing the orientational ordering of the liquid crystal at the surface. In performing the method, a continuous change in the orientational ordering of the liquid crystal at the liquid crystal surface indicates that the cleaning process is working, and the rate of said change in orientational ordering, the extent of said change in orientational ordering, or both, are correlated with the overall effectiveness of the cleaning process.

In some embodiments, the liquid crystal is a low molecular weight liquid crystal, a liquid crystal elastomer, a liquid crystalline gel, a liquid crystal droplet, or a liquid crystal composite. In some such embodiments, the low molecular weight liquid crystal comprises nematic 4'-pentyl-4-cyanobiphenyl (5CB).

In some embodiments, the cleaning solution includes a detergent, a polymer, a lipid, an enzyme, or a mixture thereof. In some such embodiments, the enzyme is a protease.

In some embodiments, the one or more proteins adsorbed to the liquid crystal surface are selected from streptavidin, conjugated streptavidin, and anti-biotin antibody.

In some embodiments, the step of observing the orientational ordering of the liquid crystal at the surface is performed by detecting polarized light that is passed through the interface. Optionally, the polarized light is passed through the interface between crossed polarizers.

In some embodiments, the step of observing the orientational ordering of the liquid crystal at the surface includes calculating the tilt angle of the liquid crystal at the interface relative to the interface normal, wherein the tilt angle indicates the extent of the change in orientational ordering. Optionally, the tilt angle is calculated from the effective birefringence of the liquid crystal under light illumination.

In a third aspect, the disclosure encompasses a method for assaying the effectiveness of a putative protein stabilizing agent. The method includes the steps of (a) providing one or more proteins and a putative protein stabilizing agent at an interface between an aqueous phase and a liquid crystal phase; (b) aging the interface and associated proteins; (c) contacting the interface with a protein removing agent; and (d) observing the orientational ordering of the liquid crystal at the interface. In performing the method, the rate of change in the orientational ordering, the extent of change in the orientational ordering, or both, is correlated with the effectiveness of the putative protein stabilizing agent.

In some embodiments, the liquid crystal phase includes a low molecular weight liquid crystal, a liquid crystal elastomer, a liquid crystalline gel, or a liquid crystal droplet. In some such embodiments, the low molecular weight liquid crystal comprises nematic 4'-pentyl-4-cyanobiphenyl (5CB).

In some embodiments, the protein removing agent is a detergent, a surfactant, a lipid, an enzyme, or a mixture thereof. In some such embodiments, the enzyme is a protease.

In some embodiments, the step of observing the orientational ordering of the liquid crystal at the interface is performed by detecting polarized light that is passed through the interface. Optionally, the polarized light is passed through the interface between crossed polarizers.

In some embodiments, the step of observing the orientational ordering of the liquid crystal at the surface comprises calculating the tilt angle of the liquid crystal at the interface relative to the interface normal, wherein the tilt angle indicates the extent of the change in orientational ordering. Optionally, the tilt angle is calculated from the effective birefringence of the liquid crystal under light illumination.

In a fourth aspect, the disclosure encompasses a method for assaying the optimal concentration of a protein for preventing the unfolding of the protein. The method includes the steps of (a) providing one or more proteins at a known concentration at an interface between an aqueous phase and a liquid crystal phase; (b) aging the interface and associated proteins; (c) contacting the interface with a protein removing agent; and (d) observing the orientational ordering of the liquid crystal at the interface. In performing the method, the rate of change in the orientational ordering, the extent of change in the orientational ordering, or both, is correlated with the effectiveness of the known concentration for preventing the unfolding of the protein.

In some embodiments, the liquid crystal phase is comprised of a low molecular weight liquid crystal, a liquid crystal elastomer, a liquid crystalline gel, or a liquid crystal droplet. In some such embodiments, the low molecular weight liquid crystal includes nematic 4'-pentyl-4-cyanobiphenyl (5CB).

In some embodiments, the protein removing agent is a detergent, a surfactant, a lipid, an enzyme, or a mixture thereof. In some such embodiments, the enzyme is a protease.

In some embodiments, the step of observing the orientational ordering of the liquid crystal at the interface is performed by detecting polarized light that is passed through the interface. Optionally, the polarized light is passed through the interface between crossed polarizers.

In some embodiments, the step of observing the orientational ordering of the liquid crystal at the surface includes calculating the tilt angle of the liquid crystal at the interface relative to the interface normal, wherein the tilt angle indicates the extent of the change in orientational ordering. Optionally, the tilt angle is calculated from the effective birefringence of the liquid crystal under light illumination.

In a fifth aspect the disclosure encompasses a device for assaying the effectiveness of a cleaning agent or a putative protein stabilizing agent. The device includes an interface between an aqueous phase and a liquid crystal phase that includes one or more proteins and further includes a cleaning agent or a putative protein stabilizing agent. In the device, the interface exhibits a continuous orientation ordering tilt angle relative to the interface normal that is intermediate between planar (parallel to the interface) and homeotropic (perpendicular to the interface).

In some embodiments, the liquid crystal phase includes a low molecular weight liquid crystal, a liquid crystal elastomer, a liquid crystalline gel, or a liquid crystal droplet. In some such embodiments, the low molecular weight liquid crystal includes nematic 4'-pentyl-4-cyanobiphenyl (5CB).

In some embodiments, the cleaning agent is a detergent, a polymer, a lipid, an enzyme, or a mixture thereof. In some such embodiments, the enzyme is a protease.

In some embodiments, the one or more proteins are selected from streptavidin, conjugated streptavidin, and anti-biotin antibody.

In some embodiments, the tilt angle is between 10° and 80° relative to the interface normal. In some such embodiments, the tilt angle is between 30° and 60° relative to the interface normal.

In a sixth aspect, the disclosure encompasses a method for assaying the optimal concentration of an agent that prevents the fouling of an interface by one or more proteins. The method includes the steps of (a) providing one or more proteins and a putative agent that prevents fouling of an interface by proteins at an interface between an aqueous phase and a liquid crystal phase; (b) contacting the interface with a protein imaging agent; and (c) observing the orientational ordering of the liquid crystal at the interface. In performing the method, the rate of change in the orientational ordering, the extent of change in the orientational ordering, or both, is correlated with the effectiveness of the known concentration for preventing the unfolding of the protein. In some embodiments, the protein imaging agent is a detergent, a polymer, a lipid, a mixture thereof.

Further objects, features and advantages of the invention will be apparent from the following detailed description when taken in conjunction with the accompanying drawings.

BRIEF DESCRIPTION OF THE DRAWINGS

The disclosure will be better understood and features, aspects and advantages other than those set forth above will become apparent when consideration is given to the following detailed description thereof. Such detailed description makes reference to the following drawings.

Figure 1:
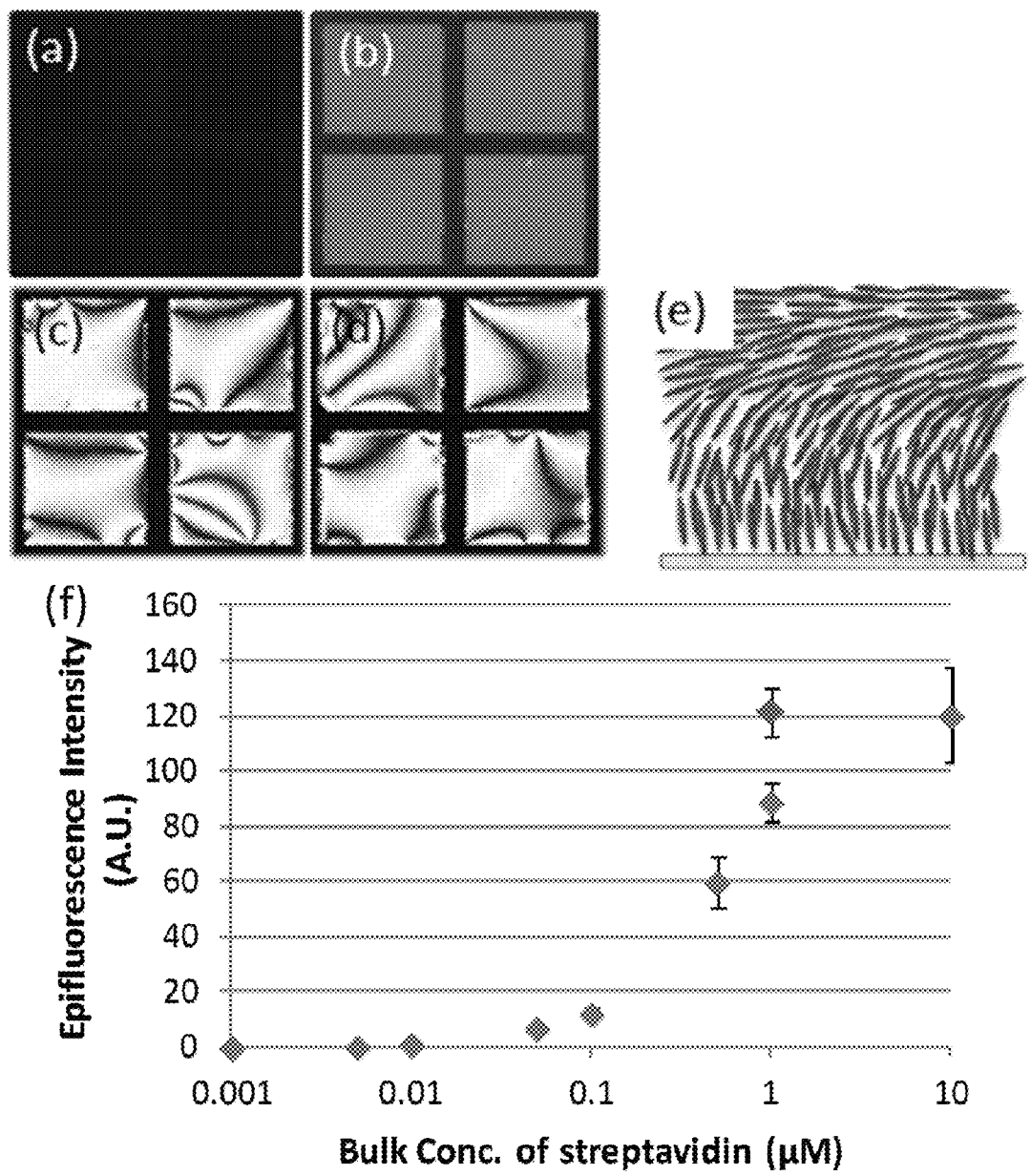
FIG. 1. Epifluorescence micrographs of an aqueous-5CB interface following incubation against (a) aqueous buffer (0.5 mM PBS) or (b) 1 µM streptavidin in aqueous solution (1 mol % Texas-Red-conjugated streptavidin). Corresponding optical micrographs (crossed polarizers) of the nematic 5CB film are shown in (c) and (d) respectively. (e) Schematic illustration of the director profile of the LC corresponding to the optical images shown in (c) and (d). (f) Plot of epifluorescence intensity of Texas Red-conjugated streptavidin at the aqueous-LC interface after incubation against the indicated concentration of streptavidin in aqueous solution for 90 min (blue diamonds). The red diamond indicates the epifluorescence intensity of a LC interface that was incubated against 1 µM streptavidin for 24 h.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

I. In General

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

Nematic liquid crystals are materials with mobilities characteristic of liquids, but that are capable of organizing over distances of hundreds of micrometers. Past theoretical and experimental studies have established that the orientations of liquid crystals near an interface to a confining medium are dictated by the chemical and topographical structure of that interface. This so-called anchoring of liquid crystals by surfaces has found widespread use in the display industry and underlies the principles that are being developed for the detection of molecular and biomolecular events at interfaces. Specifically, a change in the chemical or topographical structure of an interface brought about by a chemical or biological species at a surface can give rise to new orientations of liquid crystals in contact with that surface. As liquid crystals are birefringent, these new orientations can be visualized under simple polarized microscopy.

This disclosure is based on the inventors' surprising discovery that when exposed to a cleaning agent such as a lipid, proteins decorating an aqueous-liquid crystal interface are continuously removed from the interface, leading to a continuous change in the orientational order of the liquid crystal at the interface from the initial planar orientation to a homeotropic orientation. The continuous change in orientation is manifested by a gradual change in tilt angle relative to the surface normal over time, rather than a discrete switch from the planar to the homeotropic orientation. More effective surface cleaning agents or methods will facilitate a faster change in orientation. Furthermore, as the protein ages (and becomes unfolded and cross-linked), it becomes more difficult to remove from the interface, and as the protein becomes more crowded at the interface (and thus cannot unfold as easily), it becomes easier to remove from the interface. Accordingly, in general, the disclosure encompasses methods and devices for assaying surface cleaning agents and surface cleaning processes, as well as for assaying putative protein stabilizing agents and optimal protein concentrations to prevent protein unfolding.

Thus, the inventors have developed a method for detecting the displacement of biomolecules and other adsorbed species from liquid crystal surfaces. The adsorbed species are not limited to biological molecules but includes synthetic molecules such as polymers. The adsorbed species are also not limited to biomolecules, but can be envisaged to include assemblies of biomolecules such as bacteria and viruses and extracellular matrices produced by living cells. The adsorbed species can be displaced by surfactants and lipids, causing an ordering transition in the liquid crystal. When a biomolecule (e.g., protein) or species of interest is adsorbed to the surface, the liquid crystals take on a planar alignment oriented parallel to the surface. The coated surface appears bright when interrogated with plane-polarized light. Addition of a surfactant or lipid, at an effective concentration, causes the adsorbed molecule to be displaced from the liquid crystal surface, resulting in a reorientation of the liquid crystals from planar to homeotropic alignment (i.e. perpendicular to the surface). After reorientation, the surface appears dark when interrogated with plane-polarized light.

For proteins in particular, the inventors observed that the displacement is highly dependent on the crowding and aging of the protein coated surface—with increasing time, the proteins become more difficult to remove. The inventors believe that this is due to the unfolding of the proteins into a continuous, sheet-like structure. However, when the density of the protein on the surface is increased or an additive is used, protein unfolding is inhibited, thereby mitigating the effect of time-on-surface as a factor in the removal of proteins.

The disclosed methods and devices provide a rapid and facile method to screen for the removal of protein films, other biomolecules, and biofilms from surfaces using candidate cleaning formulations comprised of surfactants, enzymes, and other bioactive compounds. Removal of the surface contaminant is accompanied by an easily visualized ordering transition in the liquid crystal—enabling parallel and high-throughput screening of formulations for optimization. As would be appreciated by those skilled in the art, transduction of the change in orientation of the LC is not limited to the use of optical methods but can include electrical methods such as measurements of electrical capacitance.

The disclosed methods and devices also provide a facile method to report changes in the states of proteins and other biomolecules bound at interfaces. The method can be used to screen for additives that inhibit the adsorption and unfolding of proteins at hydrophobic surfaces that could then be used to stabilize proteins during storage. In addition, this method could be used to identify critical concentrations of biomolecules and proteins that limit their ability to unfold/interact to form continuous, sheet-like structures. The method can also be used to detect the folded states of proteins in solution by adsorbing the proteins in different folded states onto the interface of the LC and probing their ease of removal by addition of amphiphiles.

Applications of these methods include, but are not limited to, examining how surface properties impact the adsorption of and removal of proteins; screening proteases to determine their effectiveness as cleaners for removing proteins from surfaces; assessment of cleaning solutions in removing biofilms from surfaces; high-throughput screening of consumer/commercial cleaning solutions; validation of cleaning processes; and analyzing surface interactions for stabilization of protein therapeutics.

In a first aspect, the disclosure encompasses a method for assaying the effectiveness of a cleaning composition in removing a protein or a biofilm from a surface. The method includes the steps of providing one or more proteins at an interface between an aqueous phase and a liquid crystal phase; contacting the interface with a cleaning composition; and observing the orientational ordering of the liquid crystal at the interface. A change in the orientational ordering of the liquid crystal at the interface indicates that the proteins are being removed from the interface. The rate of the change in orientational ordering, the extent of the change in orientational ordering, or both, are correlated with the effectiveness of the cleaning composition in removing a protein or a biofilm from a surface.

In a second aspect, the disclosure encompasses a method for validating a cleaning process. The method includes the steps of contacting a cleaning solution with a surface to be cleaned; adding a liquid crystal having one or more proteins adsorbed to the liquid crystal surface to the cleaning solution; and observing the orientational ordering of the liquid crystal at the surface. A change in the orientational ordering of the liquid crystal at the liquid crystal surface indicates that the cleaning process is working, and the rate of the change in orientational ordering, the extent of the change in orientational ordering, or both, are correlated with the overall effectiveness of the cleaning process.

In a third aspect, the disclosure encompasses a method for assaying the effectiveness of a putative protein stabilizing agent. The method includes the steps of providing one or more proteins and a putative protein stabilizing agent at an interface between an aqueous phase and a liquid crystal phase; aging the interface (by, for example, letting it sit for a day), contacting the interface with a protein removing agent, such as a detergent, lipid, surfactant, or enzyme; and observing the orientational ordering of the liquid crystal at the interface. The rate of change in the orientational ordering, the extent of change in the orientational ordering, or both, is correlated with the effectiveness of the putative protein stabilizing agent.

In a fourth aspect, the disclosure encompasses a method for assaying the optimal concentration of a protein for preventing the unfolding of the protein. The method includes the steps of providing one or more proteins at a known concentration at an interface between an aqueous phase and a liquid crystal phase; aging the interface (by, for example, letting it sit for a day); contacting the interface with a protein removing agent, such as a detergent, lipid, surfactant, or enzyme; and observing the orientational ordering of the liquid crystal at the interface. The rate of change in the orientational ordering, the extent of change in the orientational ordering, or both, is correlated with the effectiveness of the known concentration for preventing the unfolding of the protein.

In a fifth aspect, the disclosure encompasses a device for assaying the effectiveness of a cleaning agent or a putative protein stabilizing agent. Such a protein stabilizing agent might be a sugar or another water soluble molecule. The device includes an interface between an aqueous phase and a liquid crystal phase that includes one or more proteins and further includes a cleaning agent or a putative protein stabilizing agent. The liquid crystal at the interface exhibits a continuous orientation ordering tilt angle relative to the interface normal that is intermediate between planar (parallel to the interface) and homeotropic (perpendicular to the interface).

In a sixth aspect, the disclosure encompasses a method for assaying the optimal concentration of an agent that prevents the fouling of an interface by one or more proteins. The method includes the steps of providing one or more proteins and a putative agent that prevents fouling of an interface by proteins at an interface between an aqueous phase and a liquid crystal phase; contacting the interface with a protein imaging agent; and observing the orientational ordering of the liquid crystal at the interface. In performing the method, the rate of change in the orientational ordering, the extent of change in the orientational ordering, or both, is correlated with the effectiveness of the known concentration for preventing the unfolding of the protein. In some embodiments, the protein imaging agent may be a detergent, a polymer, a lipid, or a mixture thereof.

In certain embodiments of the disclosed methods and devices, the liquid crystal phase can include a low molecular weight liquid crystal, a liquid crystal elastomer, a liquid crystalline gel, or a liquid crystal droplet. The liquid crystal may also contain a chiral additive to create a cholesteric phase. The term "liquid crystal", as used herein, refers to an organic composition in an intermediate or mesomorphic state between solid and liquid. Suitable liquid crystals for use in the present invention include, but are not limited to, thermotropic liquid crystals. The disclosed methods and devices may employ polymeric liquid crystals, composite materials comprising particles and liquid crystals, or polymers and liquid crystals, as well as elastomeric liquid crystals. The invention may also use of liquid crystalline gels, including colloid-in-liquid crystal gels and molecular liquid crystalline gels containing, for example, gelators comprised of derivatives of amino acids.

An example of a liquid crystalline elastomer is synthesized from the mesogen $M_4OCH_3$ and polymethylhydrosiloxane, according to A. Komp and coworkers "A versatile preparation route for thin free standing liquid single crystal elastomers" *Macromol. Rapid Commun,* 26: 813-818, 2005. Other LC elastomers suitable for use in the current disclosure are described by Deng in "Advances in liquid crystal elastomers", *Progress in Chemistry,* 18 (10): 1352-1360, 2006, and references cited therein. The scope of the disclosure also includes use of liquid crystalline hydrogels, as described by Weiss, F. and Finkelmann H. in *Macromolecules;* 37(17); 6587-6595, 2004, and references cited therein. Other embodiments use a composite comprising a dispersion of solid particulates, such as but not limited to microspheres, mixed with liquid crystal. Such composites are known by those skilled in the art to form a gel.

Other classes of liquid crystals that may be used in accordance with the invention include, but are not limited to: polymeric liquid crystals, thermotropic liquid crystals, lyotropic liquid crystals, columnar liquid crystals, nematic discotic liquid crystals, calamitic nematic liquid crystals, ferroelectric liquid crystals, discoid liquid crystals, and cholesteric liquid crystals. Examples of just some of the liquid crystals that may be used are shown in Table 1. In some embodiments, the liquid crystal is a nematic liquid crystal such as 4-pentyl-4'-cyanobiphenyl (5CB):

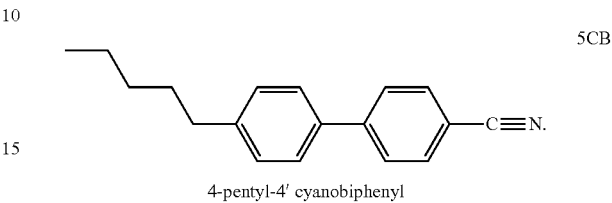

4-pentyl-4' cyanobiphenyl

TABLE 1

Molecular Structure of Mesogens Suitable for Use in the Disclosed Methods and Devices.

| Mesogen | Structure |
|---|---|
| Anisaldazine | $CH_3$—O—⟨⟩—CH=N—N=CH—⟨⟩—O—$CH_3$ |
| NCB | $C_nH_{2n+1}$—⟨⟩—⟨⟩—CN |
| CBOOA | $C_9H_{19}$—O—⟨⟩—N=CH—⟨⟩—CN |
| Comp A | $C_7H_{15}$—⟨⟩—⟨⟩—COO—⟨⟩—NCS |
| Comp B | $C_8H_{17}$—O—⟨⟩—O—CO—⟨⟩—O—$CH_2$—⟨⟩—CN |
| $DB_7NO_2$ | $C_7H_{15}$—⟨⟩—O—CO—⟨⟩—O—CO—⟨⟩—$NO_2$ |
| DOBAMBC | $C_{10}H_{21}$—O—⟨⟩—CH=N—⟨⟩—CH=CH—COO—$CH_2$—CH($CH_3$)($C_2H_5$) |
| nOm<br>n = 1, m = 4: MBBA<br>n = 2, m = 4: EBBA | $C_nH_{2n+1}$—O—⟨⟩—CH=N—⟨⟩—$C_mH_{2m+1}$ |
| nOBA<br>n = 8: OOBA<br>n = 9: NOBA | $C_nH_{2n+1}$—O—⟨⟩—COOH |
| nmOBC | $C_nH_{2n+1}$—O—CO—⟨⟩—⟨⟩—O—$C_mH_{2m+1}$ |

TABLE 1-continued

Molecular Structure of Mesogens Suitable for Use in the Disclosed Methods and Devices.

| Mesogen | Structure |
|---|---|
| nOCB | 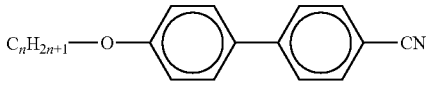 |
| nOSI | 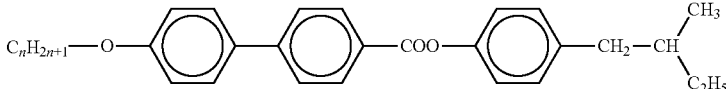 |
| 98P | 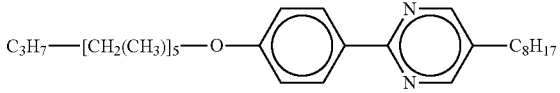 |
| PAA | 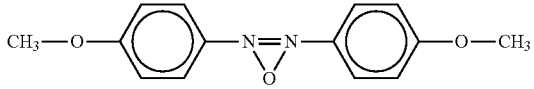 |
| PYP906 | 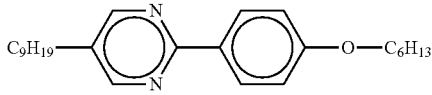 |
| $\bar{n}$Sm | 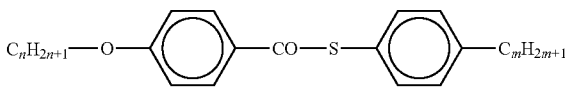 |

The disclosed methods and devices can be used to assay a wide range of cleaning compositions and processes, including without limitation those including or using detergents, polymers, surfactants, lipids, enzymes, or a mixtures thereof. Preferred agents or processes tested are those designed to remove proteins or biofilm from a surface. In certain embodiments, the cleaning agent that is tested is a lipid, such as a phospholipid. A non-limiting example of a phospholipid that could be used is dilauralphosphatidylcholine (DLPC). A non-limiting example of an enzyme that could be used is a protease.

As used herein, the term "protein" refers to a compound comprising multiple amino acid groups joined together through peptide bonds in which the carboxylic acid group of one amino acid reacts with an amine group of a second amino acid to form the amide peptide bond. In some embodiments, the proteins used in the disclosed methods and devices are selected from streptavidin, conjugated streptavidin, and anti-biotin antibody.

As used herein, the term "biofilm" refers to an aggregate of microorganisms that adhere to each other on a surface. These adherent cells are sometimes embedded within a self-produced matrix of extracellular polymeric substance (EPS), a polymeric conglomeration generally composed of extracellular DNA, proteins, and polysaccharides. Biofilms may form on both natural and synthetic surfaces, and are a common problem in industrial and hospital settings.

As is known to those skilled in the art, changes in the orientational order of the liquid crystal can lead to a change in the optical properties of the liquid crystal. Such changes can be detected and quantified by using optical instrumentation such as, but not limited to, plate readers, cameras, scanners, and photomultiplier tubes. Because the dielectric properties of liquid crystals also change with orientational order, measurements of electrical properties of liquid crystals can also be used to report changes in the orientational order of the liquid crystals. Thus a wide range of optical and electrical methods for observing the change in orientational order of liquid crystals is anticipated by this disclosure.

For example, in certain embodiments, the step of observing the orientational ordering of the liquid crystal at the interface is performed by detecting plane polarized light that is passed through the interface or liquid crystal surface. In some such embodiments, the plane polarized light is passed through the interface between crossed polarizers. Homeotropic ordering can be shown by observing the absence of transmitted light between cross-polarizers, and can be confirmed by an interference pattern consisting of two crossed isogyres under conoscopic examination. Planar ordering results in bright colored appearance when viewed between cross-polarizers.

In certain embodiments of the disclosed methods and devices, the orientational ordering of the liquid crystal undergoes continuous change over time, as the protein is removed from the interface or liquid crystal surface. Thus, there is a transitional orientational ordering state between the planar orientation (parallel to the LC interface or surface) and the homeotropic orientation (perpendicular to the LC interface or surface). The transitional ordering is indicated by the so-called "tilt angle," which is the angle at which the LC is oriented as compared to the surface normal (a vector perpendicular to the surface). As protein is removed from the interface or LC surface, the tilt angle is seen to decrease, as the LC continuously transitions from the planar to the homeotropic orientation.

In certain embodiments, the step of observing the orientational ordering of the liquid crystal at the interface comprises calculating the tilt angle of the liquid crystal at the interface relative to the interface normal. The change in the tilt angle over time indicates the extent of the change in orientational ordering. Methods of calculating the tilt angle are not limited, and include using the effective biofringence of the liquid crystal under white light illumination.

In such embodiments, the color of the LC under white-light illumination can be matched against a Michel-Levy chart to determine the effective birefringence $\Delta n_{eff}$ of a LC film of known thickness. For each value of $\Delta n_{eff}$, the tilt angle at an aqueous-LC interface (measured relative to the surface normal), $\theta$, can be determined by, for example, solution of the equation:

$$\Delta n_{eff} \approx \frac{1}{d} \int_0^d \left( \frac{n_\| n_\perp}{\sqrt{n_\perp^2 \sin^2\left(\frac{z}{d}\theta\right) + n_\|^2 \cos^2\left(\frac{z}{d}\theta\right)}} - n_\perp \right) dz,$$

where $n_\|$ and $n_\perp$ are the indices of refraction parallel and perpendicular to the optical axis of the LC, respectively, and d is the thickness of the LC film.

In certain embodiments, the disclosure includes LC tilt angles of between 10° and 80° relative to the interface normal. In some such embodiments, the tilt angle is between 30° and 60° relative to the interface normal. Such angles show continuous transition of orientational ordering, in contrast to the discontinuous and discrete transitions that characterize some other LC-based systems and methods.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1

Ordering Transitions Triggered by the Binding of Vesicles to Protein-Decorated Liquid Crystal Interfaces Summary.

We report that specific binding of ligand-functionalized (biotinylated) phospholipid vesicles (diameter=120±19 nm) to a monolayer of proteins (streptavidin or anti-biotin antibody) adsorbed at an interface between an aqueous phase and an immiscible film of a thermotropic liquid crystal (LC) (nematic 4'-pentyl-4-cyanobiphenyl (5CB)) triggers a continuous orientational ordering transition (continuous change in the tilt) in the LC. Results presented in this example indicate that, following the capture of the vesicles at the LC interface via the specific binding interaction, phospholipids are transferred from the vesicles onto the LC interface to form a monolayer, reorganizing and partially displacing proteins from the LC interface. The dynamics of this process are accelerated substantially by the specific binding event relative to a protein-decorated interface of a LC that does not bind the ligands presented by vesicles.

The observation of the continuous change in the ordering of the LC, when combined with other results presented in this example, is significant as it is consistent with the presence of sub-optical domains of proteins and phospholipids on the LC interface. An additional significant hypothesis that emerges from the work reported in this example is that the ordering transition of the LC is strongly influenced by the bound state of the protein adsorbed on the LC interface, as evidenced by the influence on the LC of (i) "crowding" of the protein within a monolayer formed at the LC interface and (ii) aging of the proteins on the LC interface. Overall, these results demonstrate that ordering transitions in LCs can be used to provide fundamental insights into the competitive adsorption of proteins and lipids at oil-water interfaces, and that LC ordering transitions have the potential to be useful for reporting specific binding events involving vesicles and proteins.

Introduction.

Past studies have established that ordering transitions in thermotropic liquid crystals (LCs) can be triggered by the adsorption and organization of amphiphiles and polymers at interfaces between nematic LCs and immiscible aqueous phases.[1-5] The surface energetics that control these ordering transitions are remarkably delicate, typically on the order of 1-10 $\mu J/m^2$,[6] thus leading to LC interfacial phenomena that are dependent on the details of the organization of the adsorbates. In addition, because molecules within LC phases are correlated in their orientations over distances of micrometers,[7] surface-induced ordering transitions in LCs can propagate into the bulk of the LC phases, enabling the reporting of interfacial events through measurements of changes in bulk LC properties (e.g., optical retardance).[8]

The assembly of synthetic surfactants and biological lipids at aqueous-LC interfaces has received particular attention in recent studies.[1] For this class of adsorbates, the steric interactions of the tails of the amphiphiles and the mesogens of the thermotropic LC have been shown to couple the interfacial organization of the amphiphiles to the orientational ordering of the LC.[9-14] For example, contact of an aqueous dispersion of vesicles of dilauroylphosphatidylcholine (DLPC) with the interface of a micrometer-thick film of nematic 4'-pentyl-4-cyanobiphenyl (5CB) has been observed to result in spontaneous formation (via fusion) of a monolayer of DLPC on the interface of the LC, resulting in a discontinuous orientational ordering transition in which the LC changes from an orientation that is parallel to the interface (prior to lipid adsorption) to perpendicular to the interface (after lipid adsorption).[9] In addition, it was observed that, at interfacial densities of DLPC below saturation coverage, the DLPC monolayer exhibited coexisting lipid-rich and lipid-lean domains which gave rise to patterned orientations of the LC.[9,15] A series of subsequent studies established that the phase separation of the DLPC at the interface of the LC was driven by the release of elastic energy stored in the initially strained state of the micrometer-thick film of LC, indicating that LCs should not, in general, be viewed as passive reporters of interfacial phenomena but that they can also be used to direct molecular assembly processes at their interfaces.[15-17]

All of the studies described above revolve around the adsorption of lipids at unmodified interfaces between aqueous phases and LCs,[9-11,15] in which case the adsorption of the lipids is driven largely by hydrophobic interactions with the LC. In contrast, in this example, we move to examine the interactions of phospholipids with protein-decorated interfaces of the LC. Specifically, we sought to determine if specific binding of ligand-functionalized phospholipid vesicles to proteins pre-adsorbed at the aqueous-LC interface would facilitate transfer of phopholipids onto the interface of the LC and thus trigger an ordering transition in the LC. The majority of the experiments reported in this example were performed with a model system comprised of the protein streptavidin adsorbed onto the aqueous interface of nematic 5CB, and vesicles composed of mixtures of DLPC and biotin-DOPE. In addition, however, we also present experimental results that demonstrate that the principles established using this model system do extend to antibody (IgG)-decorated interfaces of the LC.

Whereas specific binding of phospholipid vesicles to proteins attached at the surfaces of solids has been the subject of a number of past studies,[18-22] the experimental system reported in this paper differs from those past studies in several key ways. First, in our experimental system, the LC interface onto which the proteins are adsorbed is mobile and deformable.[10,23] Thus, upon capture of the vesicles, the proteins and phospholipids at the LC interface are able to reorganize laterally in ways that are not possible at the surfaces of solids. Second, and importantly, the ordering of the LC in our experiments responds to the composition and organization of the proteins and phospholipids captured at the LC interface. In this context, we comment that the interface of a nematic LC is a particularly interesting one because past studies have demonstrated that the influence of adsorbed proteins or lipids on the ordering of the LC is antagonistic.[18,24] That is, whereas the interaction of the tails of many lipids (lipids with unbranched tails[12,13]) with LCs tends to promote homeotropic (perpendicular) ordering of the LCs (as described above),[9,10] past studies have also established that proteins adsorbed to the interfaces of LCs promote planar anchoring of the LCs.[25-27] In the experiments reported in this example, we investigated how the competitive interactions of proteins and phopholipids at LC interfaces influence the ordering of LCs.

A central result of the study reported in this example is that we observe nematic phases of 5CB to undergo continuous ordering transitions (continuous change in the tilt of the LC) upon specific binding of vesicles of phospholipid to protein-decorated interfaces of LC. Our results indicate that, following capture of vesicles at the LC interface via specific binding interactions, phospholipids are transferred from the vesicles onto the LC interface, reorganizing and partially displacing proteins from the LC interface. As discussed later in this example, the observation of the continuous change in the ordering of the LC is consistent with the presence of small domains of proteins and phospholipids on the interface.[28]

An additional significant hypothesis that emerges from the work reported in this example is that the ordering transition of the LC appears to be influenced by the state of the protein adsorbed on the LC interface, as evidenced by the influence on the LC of (i) "crowding" of the protein at the LC interface, and (ii) aging of the protein at the LC interface. Overall, these results demonstrate that ordering transitions in LCs can be used to provide fundamental insights into the competitive adsorption of proteins and lipids at oil-water interfaces, and that the LC ordering transitions have the potential to be useful for reporting specific binding events involving vesicles and proteins. In this context, we note that native vesicles shed by mammalian cells are a largely unexplored source of biological information regarding the states of cells, and that a need exists for analytic methods capable of compositional analysis of native microvesicles.[29,30] The interfacial phenomena reported in this example hints at principles that may form the basis for such methods using LCs.

Experimental Section.

Materials.

Tris-buffered saline (TBS) (0.05 M TRIS; 0.138 M NaCl; 0.0027 M KCl; pH 8.0), phosphate-buffered saline (PBS) (0.01M phosphate; 0.138 M NaCl; 0.0027 M KCl; pH 7.4), octyltrichlorosilane (OTS), anti-biotin antibody (produced in goat) and anti-goat IgG antibody were obtained from Sigma-Aldrich (St Louis, Mo.). Streptavidin, Texas Red-conjugated streptavidin, and N-(4,4-difluoro-5,7-dimethyl-4-bora-3a, 4a-diaza-s-indacene-3-propionyl)-1,2-dihexadecanoyl-sn-glycero-3-phosphoethanolamine triethylammonium salt (BODIPY-DHPE) were obtained from Molecular Probes (Eugene, Oreg.). 1,2-dilauroyl-sn-glycero-3-phosphocholine (DLPC) and 1,2-dioleoyl-sn-glycero-3-phosphoethanolamine-N-(biotinyl) (biotin-DOPE) were purchased from Avanti Polar Lipids, Inc (Alabaster, Ala.). 2-propanol and Fisher's Finest Premium Grade glass slides were purchased from Fisher Scientific (Pittsburgh, Pa.). Gold specimen grids (20 µm thickness, 283 µm grid spacing, and 50 µm bar width) were obtained from Electron Microscopy Sciences (Fort Washington, Pa.). The nematic LC 4'-pentyl-4-cyanobiphenyl was obtained from EMD Chemicals (Spring Valley, N.Y.). Deionization of a distilled water source was performed with a Milli-Q system (Millipore, Bedford, Mass.) to give water with a resistivity of 18.2 MΩ-cm.

Methods.

Preparation of Protein-Decorated Interfaces of Nematic 5CB.

A detailed description of the method used to prepare micrometer-thick films of LC hosted within gold specimen grids can be found in a previous publication.[23] Briefly, glass microscope slides were cleaned according to published procedures and coated with OTS.[18] Gold specimen grids were placed onto the surface of the OTS-treated glass slides. The grids were filled with 5CB using a blunt-tipped glass syringe and the excess LC was removed such that the grid was uniformly filled with LC. The quality of the OTS layer was assessed by checking the alignment of a film of 5CB confined between OTS-treated glass and air. The LC-impregnated grid supported on an OTS-treated glass slide was immersed in a dish of deionized water. Formation of an adsorbed layer of protein on the interface of the LC was accomplished by introducing a solution of streptavidin (1 mg/mL in PBS) into the deionized water in contact with the interface of 5CB. The interface of the LC was incubated against the protein solution for 90 min. At the end of the equilibration period, free streptavidin in the bulk aqueous solution was removed by sequential exchange or dilution of the aqueous phase with deionized water.

Preparation of Phospholipid Vesicles.

Dispersions of vesicles of phospholipid were prepared using previously described methods.[18] Briefly, DLPC and biotin-DOPE (dissolved in chloroform) were dispensed into glass vials. BODIPY-DHPE (dissolved in ethanol) was added when fluorescent measurements were to be performed. The solvents were subsequently evaporated under a stream of $N_2$ and the vial containing the phospholipids was placed under vacuum for at least 1 h. The dried lipid was resuspended in an aqueous solution of TBS and then extruded several times through a polycarbonate membrane filter (pore size of 100 nm) (Millipore, Bedford, Mass.). The above-described procedure yielded unilamellar vesicles with an average diameter of 120 nm, as determined using dynamic light scattering (DLS). All phospholipid dispersions were used within 24 h of their preparation.

Interactions of Phospholipid Vesicles with Protein-Decorated Interfaces of 5CB.

After formation of protein-decorated aqueous-LC interfaces (as described above), an aliquot of a dispersion of phospholipid was added to the aqueous phase. The LC-filled grids were incubated against the dispersion of vesicles and the orientation of the nematic film of 5CB was then optically characterized according to the methods described below.

Optical Characterization of LC Ordering.

The orientation of the nematic phase of 5CB was determined by using plane-polarized light in transmission mode on an Olympus BX60 microscope with crossed polarizers. The gold grid hosting the film of 5CB was placed on a rotating stage located between polarizers. In-plane birefringence was indicated by a bright, colored appearance of the 5CB and the presence of brush textures when the sample was viewed between crossed polarizers.[31] Homeotropic alignment of the LC was determined by first observing the absence of transmitted light during a 360° rotation of the sample between crossed polarizers. Insertion of a condenser below the stage and a Bertrand lens above the stage allowed conoscopic examination of the LC film. An interference pattern consisting of two crossed isogyres confirmed homeotropic alignment.[32] All images were captured using a digital camera (Olympus C-2040 Zoom) mounted on the microscope. The camera was set to an f-stop of 2.8 and a shutter speed of 1/60 s.

Determination of the Tilt of 5CB at the Aqueous-LC Interface.

The color of the LC under white-light illumination was matched against a Michel-Levy chart to determine the effective birefringence $\Delta n_{eff}$ of the 20-μm-thick film of 5CB. For each value of $\Delta n_{eff}$, the tilt angle of 5CB at the aqueous-LC interface (measured relative to the surface normal), θ, was determined by solution of the equation:

$$\Delta n_{eff} \approx \frac{1}{d} \int_0^d \left( \frac{n_{\|} n_{\perp}}{\sqrt{n_{\perp}^2 \sin^2\left(\frac{z}{d}\theta\right) + n_{\|}^2 \cos^2\left(\frac{z}{d}\theta\right)}} - n_{\perp} \right) dz,$$

where $n_{\|}$ and $n_{\perp}$ are the indices of refraction parallel and perpendicular to the optical axis of 5CB, respectively, and d is the thickness of the LC film.[33] The indices of refraction of 5CB were taken as constant using the values reported for λ=632 nm at 25° C. ($n_o$=1.711 and $n_e$=1.5296).[34] The tilt angles reported in this paper are the average of nine different random locations of each of two independent grids.

Epifluorescence Imaging of Aqueous-5CB Interface.

Prior to examination, the aqueous phase in contact with the interface of the LC was diluted with deionized water to remove free proteins or lipids from the bulk solution. Proteins and phospholipids adsorbed at the aqueous-LC interface were imaged by epifluorescence microscopy using an Olympus IX71 inverted microscope equipped with a 100 W mercury lamp. A fluorescence filter cube with an excitation filter of 560 nm and an emission filter of 645 nm was used to image Texas Red fluorescence. BODIPY fluorescence was imaged using a fluorescence filter cube with an excitation filter of 480 nm and an emission filter of 535 nm. Images were collected with a Hamamatsu 1394 ORCA-ER-CCD camera (Bridgewater, N.J.) interfaced to a computer using SimplePCI imaging software (Compix, Inc.). Background fluorescence intensity was determined prior to contact of the LC interface with the fluorescently-labeled biomolecules and subtracted from the raw values. All fluorescence intensity measurements were determined using ImageJ (public-domain image processing software by the U.S. National Institutes of Health).

Quantification of the Interfacial Density of Phospholipid Via Fluorimetric Measurements.

Fluorimetric measurements were performed using a Fluo-roMax-3 fluorimeter (Instruments S. A./Jobin Yvon/Spex Horiba Group, Edison, N.J.) with an excitation wavelength of 480 nm (0.5 nm excitation slit) and an emission wavelength range of 490-550 nm (5 nm emission slit) for the detection of BODIPY fluorescence. The fluorimeter was connected to a computer and controlled using DATAMAX software (Instruments S. A./Jobin Yvon/Spex Horiba Group).

To determine the interfacial concentration of phospholipid at the aqueous-LC interface, the following procedure was used.[35] First, a calibration curve of fluorimetric intensity versus known lipid concentration in bulk solution was prepared by using 1 mL of 2-propanol containing known amount of phospholipids (containing 1 mol % BODIPY-DHPE). Next, phospholipid-decorated 5CB was extracted from a metal grid using a blunt-tip micro-syringe and dissolved in 1 mL of 2-propanol. Fluorimetric measurements were used to determine the amount of phospholipid in each sample. When combined with knowledge of the area of the LC interface, the above measurements were used to calculate the interfacial concentration of phospholipid in each experiment.

Results.

Adsorption of Streptavidin at Aqueous-5CB Interfaces.

While many past studies have reported that amphiphilic polymers and lipids adsorb spontaneously onto aqueous-LC interfaces[1,2] (and that proteins adsorb to isotropic oil-water interfaces[36-38]), the adsorption of proteins onto aqueous-thermotropic LC interfaces has not been widely characterized.[39] Initially, therefore, we performed a series of fluorescence measurements to determine the extent to which streptavidin adsorbs from bulk aqueous solution onto aqueous interfaces of nematic 5CB. We also investigated whether the ordering of the nematic 5CB was measurably perturbed by adsorption of the streptavidin.

In these experiments, an aqueous-5CB interface was prepared (see Methods) and incubated against a buffered (PBS) solution of streptavidin comprised of 1 mol % Texas Red-conjugated streptavidin for 90 min. The aqueous solution of streptavidin was subsequently exchanged with deionized water via sequential dilution to remove the free streptavidin from bulk solution. The resulting LC interface was imaged for Texas Red fluorescence. FIGS. 1a and 1b show fluorescent micrographs of aqueous-5CB interfaces that were incubated against either a solution free of streptavidin (FIG. 1a) or a 1 μM solution of streptavidin (FIG. 1b).

Inspection of FIGS. 1a and 1b reveals that the interface that was incubated against the solution contaning streptavidin (FIG. 1b) exhibited a fluorescence intensity that was higher than the control (FIG. 1a), confirming that streptavidin adsorbed onto the LC interface. As noted above, this result is generally consistent with past studies of protein adsorption onto oil-water interfaces.[36-38] For example, Chao and co-workers reported that the interfacial tension of a chloroform drop suspended in an aqueous phase decreased upon adsorption of streptavidin.[40] In addition, we note that the pI of streptavidin is between 5 and 6.[41] At the pH of our experiments (7.4), we expect, therefore, streptavidin to carry a net negative charge. Because the ζ-potential of a 5CB-water interface at pH 7.0 has been measured to be −50 mV,[42] the adsorption of streptavidin to the interface of 5CB, as reported above, is likely driven by forces other than electrostatic ones (e.g., hydrophobic interactions).

FIGS. 1c and 1d show polarized light micrographs of the nematic films of 5CB following contact with the aqueous solutions without or with streptavidin, respectively. These optical micrographs (crossed polars) reveal the LC to exhibit a bright and colorful optical appearance under white-light illumination.

Here, we briefly sketch the basis of our interpretation of these and other polarized light micrographs presented in this example (we refer the reader to past publications for detailed discussions[2,23]). In the experiments reported in this example, the LC is supported on and oriented perpendicular to a monolayer of OTS formed on a glass slide.[18] By using the Michel-Levy color chart to quantify the retardance of the 20-μm- thick, supported film of 5CB, the optical appearance (with pale green-pink or yellow hues) of the LC in FIG. 1c can be used to establish that the LC is anchored parallel to the aqueous-5CB interface.[32] These so-called hybrid anchoring conditions introduce splay and bend strain into the film of LC (see FIG. 1e for the director profile). We also note that a prominent feature of the optical appearance of the LC within each compartment of the metallic grid used to stabilize the film of LC is the presence of dark brushes.[43] This feature is caused by variation of the azimuthal orientation of the LC within each compartment.

A comparison of FIGS. 1c and 1d reveals that adsorption of streptavidin onto the interface of the LC does not lead to a significant change in the optical appearance of nematic 5CB (colors or defect/brush textures). This result is consistent with previous studies which have concluded that protein-decorated surfaces of solids give rise to planar orientations of nematic 5 CB.[25-27]

We also quantified the effect of the concentration of streptavidin in the bulk aqueous solution (1 mol % Texas Red-conjugated streptavidin) on the resulting density of streptavidin adsorbed onto the LC interface. FIG. 1f shows that the fluorescence intensity of Texas Red-conjugated streptavidin at the LC interface increases with increasing concentration of streptavidin within the bulk solution contacted with the LC interface (for 90 min). We sought to determine if the highest fluorescence intensity in FIG. 1f corresponded to saturation coverage. Incubation of the LC interface against 1 μM of streptavidin for 24 h did not result in an increase in epifluorescence intensity relative to the highest value reported in FIG. 1f. We interpret these results to indicate that a fluorescence intensity of 120 A.U. in FIG. 1f does correspond to saturation (monolayer) coverage. Below, we further demonstrate that the adsorption of streptavidin at these LC interfaces is irreversible (unless incubated against phospholipid).

Orientational Transitions in 5CB Induced by Specific Capture of Phospholipid Vesicles.

Following verification that the LC interfaces used in our study were decorated with streptavidin (see above), we sought to determine if capture of biotinylated vesicles via specific binding to the streptavidin-decorated interface of the LC would induce an ordering transition in the LC that is distinct from that seen when the binding groups were absent from either the vesicles or the LC interface.

Figure 2:
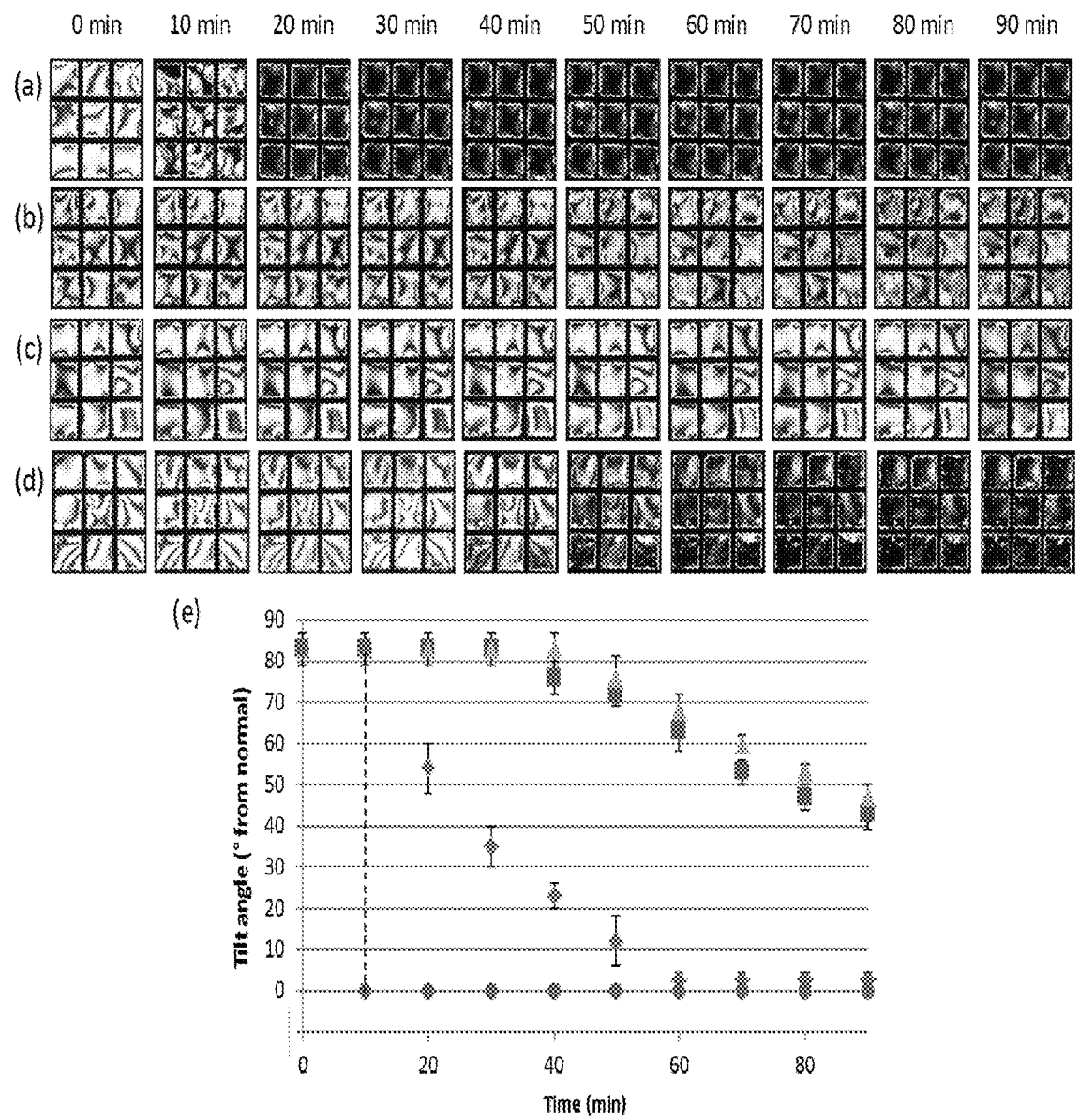
FIG. 2. Ordering transitions induced in films of nematic 5CB by incubation of vesicles (50 µM of total phospholipid concentration) against unmodified or protein-decorated aqueous interfaces of the LC. (a) Optical images (crossed polarizers) of nematic 5CB with unmodified aqueous interface (no adsorbed proteins) upon incubation against a dispersion of vesicles. (b) Optical images of 5CB with a streptavidin-decorated LC interface upon incubation against a dispersion of DLPC vesicles (no biotin-DOPE). (c) Optical images of 5CB upon incubation of a non-specific IgG-decorated interface of the LC against a dispersion of vesicles containing 5 mol % biotin-DOPE. (d) Optical images of 5CB with a streptavidin-decorated LC interface upon incubation against a dispersion of vesicles containing 5 mol % biotin-DOPE. (e) Tilt angle of 5CB at the aqueous-LC interface, plotted as a function of time following incubation against dispersions of vesicles ((a)—circles; (b)—squares; (c)—triangles; (d)—diamond).
Figure 10:
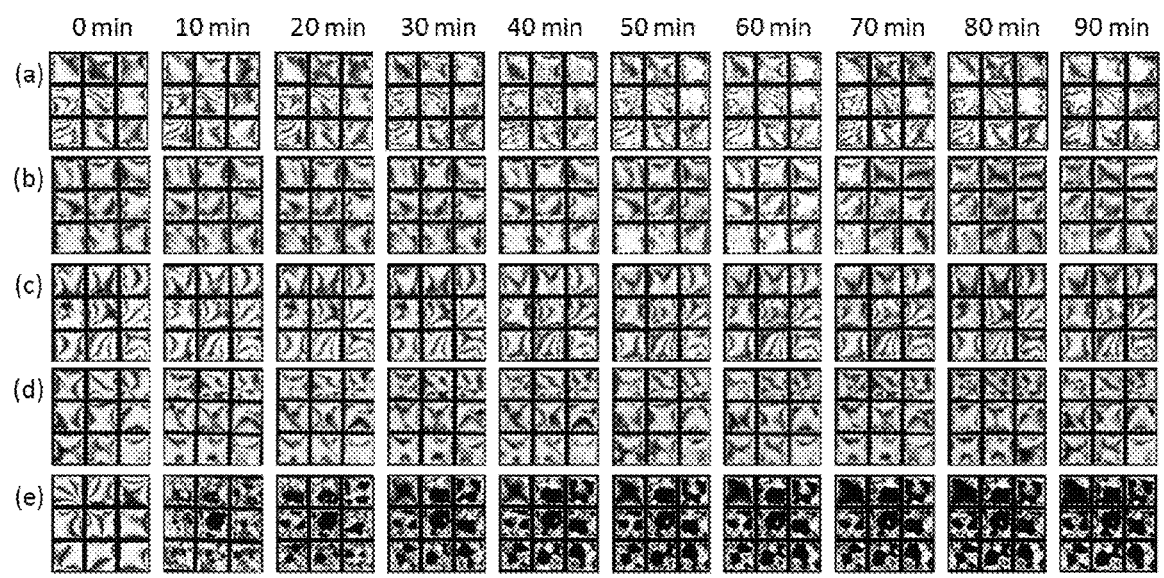
FIG. 10. Interaction of biotin-free vesicles with aqueous-LC interfaces decorated with varying interfacial density of streptavidin. Optical images (crossed polarizers) of 5CB after incubation of streptavidin-decorated interface against dispersions of vesicles (0.1 mM, 0 mol % biotin-DOPE). The interfaces were in contact with a solution of streptavidin at bulk concentrations of (a) 10, (b) 1, (c) 0.1, (d) 0.01, and (e) 0.001 µM.

In the absence of proteins bound at the LC interface (i.e., unmodified LC interface), incubation of the LC interface against a dispersion of vesicles of DLPC (no biotin-DOPE) resulted in the nucleation and growth of dark domains (when observed between crossed polars) (FIG. 2a, 10 min). The dark domains correspond to regions of homeotropic anchoring of the LC. Previous studies by Brake and co-workers attributed the homeotropic anchoring of the LC to fusion of vesicles with the interface of the LC, resulting in transfer of phospholipid onto the LC interface (FIG. 3a).[9] As noted in the Introduction, Gupta et al. subsequently showed that the elasticity of the nematic LC drives the lateral organization of the lipid on the interface into micrometer-sized domains in a manner that minimizes the elastic energy stored in the film of LC.[15]

In our experiment, a uniform dark appearance of the LC (absence of in-plane birefringence) was achieved after incubation of the LC interface against the dispersion of DLPC vesicles for 20 min (FIG. 2a). We note that each of the dark squares in the grid in FIG. 2a is framed by a bright edge. The bright edge is the result of perpendicular anchoring of the LC on the vertical walls of the grid.

Figure 3:
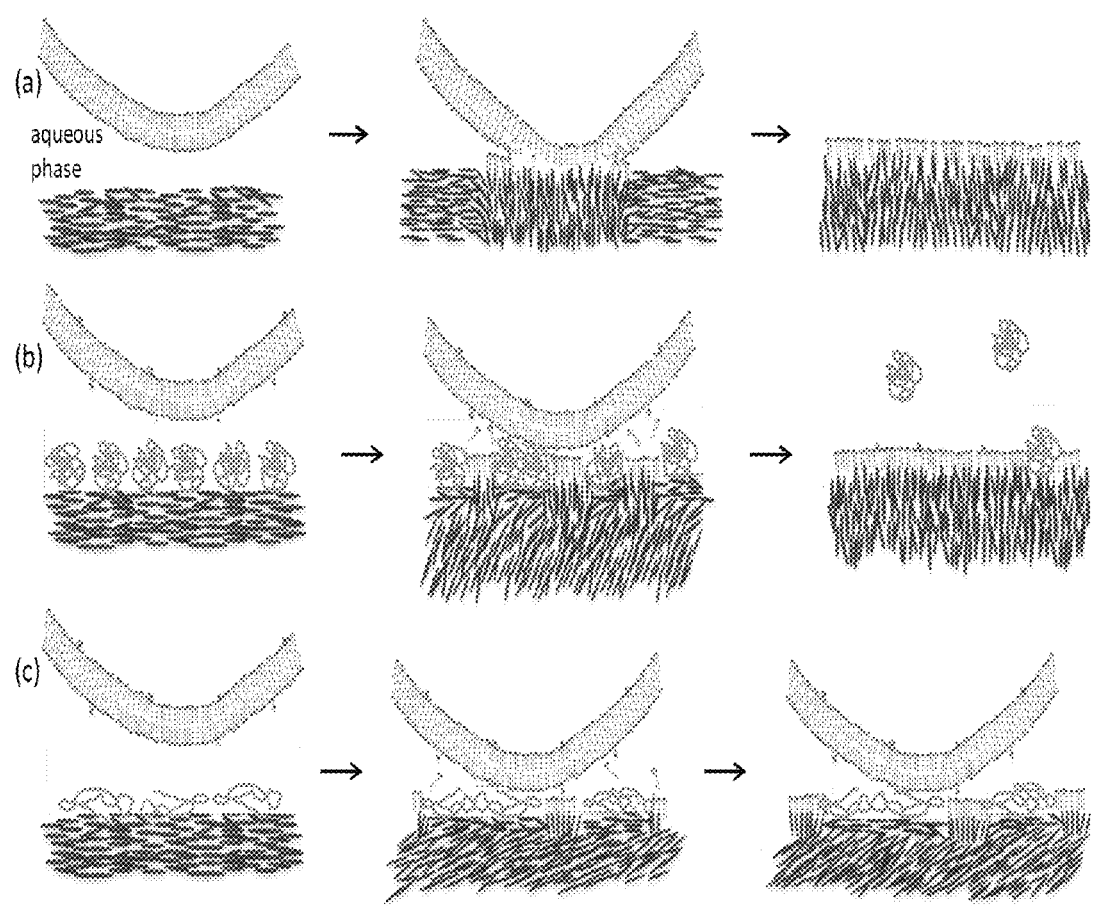
FIG. 3. (a) Schematic illustration of the anchoring of 5CB during fusion of a phospholipid vesicle onto an unmodified aqueous-LC interface. (b) Schematic illustration of a biotinylated vesicle binding to an aqueous-LC interface decorated with a high density of streptavidin, with subsequent transfer of phospholipid onto the LC interface and partial displacement of protein from the interface. (c) Schematic illustration of a biotinylated vesicle binding to an aqueous-LC interface decorated with a low density of streptavidin (or an aged protein layer). The interfacial protein unfolds on the interface, leading to a bound state on the interface that is less readily displaced by phospholipid.

Next, we determined if the presence of streptavidin adsorbed onto the LC interface would alter the dynamic ordering transition of 5CB upon exposure to a dispersion of vesicles in the absence of the biotin-DOPE binding groups within the vesicles. With streptavidin adsorbed onto the interface of the LC (from a 1 μM aqueous solution of streptavidin), incubation of the interface against a dispersion of vesicles comprised of DLPC resulted in a slow but continuous progression of interference colors (FIG. 2b), a consequence of a continuous change in the tilt of the LC at the aqueous-5CB interface over >90 min. Because the LC assumes a planar orientation at a protein-decorated interface (FIG. 1d), whereas phospholipids at the interface induce a homeotropic orientation (FIG. 2a), we interpret the tilting of the LC to reflect the competitive influence of proteins and phopholipids at the interface on the LC (FIG. 3b). Here we also note that a similar, continuous change in the tilt of the LC was observed when a dispersion of biotinylated vesicles (5 mol % biotin-DOPE) was incubated against an aqueous-5CB interface that was decorated with a protein that does not bind biotin (non-specific IgG) (FIG. 2c).

Next, we investigated if specific binding of biotinylated vesicles to the streptavidin-decorated interface of a LC would trigger an ordering transition that was distinct from the above-described cases that did not involve specific binding events. To this end, a dispersion of biotinylated vesicles containing 5 mol % biotin-DOPE was incubated against a streptavidin-decorated interface of 5CB. In the presence of the specific binding interaction, we observed a continuous transition in the orientation of the LC (FIG. 2d) with dynamics that were accelerated substantially compared to that observed in the absence of specific binding interactions (FIGS. 2b and 2c). Specifically, whereas the LC did not reach a homeotropic orientation for the latter cases for at least 90 min, homeotropic anchoring was evident within 30-40 min of incubation of biotinylated vesicles against the streptavidin-decorated aqueous-LC interface.

To quantify the difference in the orientations of the LC induced by specific and non-specific interactions of the vesicles, the interference colors generated by the LC under white-light illumination were used to determine the tilt of the LC at the aqueous interface as a function of time (FIG. 2e). These results clearly reveal that specific binding of vesicles to the protein-decorated LC interface leads to an accelerated ordering transition in the LC. Indeed, inspection of FIG. 2e reveals that the ordering transition induced by the specific binding event is almost complete prior to the onset of the ordering transition induced by non-specific interactions. Overall, we interpret these results to suggest that the biotin-mediated capture of vesicles at the LC interface serves to concentrate vesicles near the LC interface, and that following localization of the vesicles near the interface (see below for evidence of lipids at the LC interface), there is spontaneous transfer of phospholipids onto the LC interface to trigger the ordering transition. As noted above, this interpretation is supported by past studies that have shown that the presence of phospholipids at the aqueous-LC interface causes homeotropic anchoring of the LC.[9,10] As described below, however, an additional necessary process underlying the LC ordering transition is partial displacement of protein from the LC interface (by the lipids).

Figure 4:
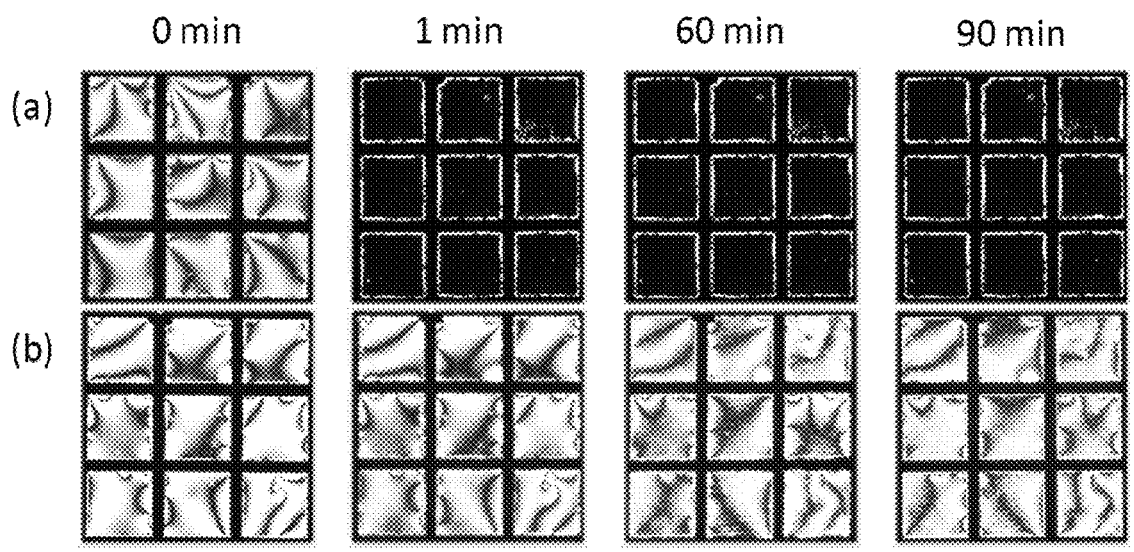
FIG. 4. Ordering transition of 5CB induced by a solution of SDS (0.1 mM) incubated against (a) an unmodified and (b) a streptavidin-decorated (from a 1 µM solution of bulk streptavidin) aqueous-LC interface.

The above results lead to two important additional conclusions. First, we conclude that the presence of streptavidin adsorbed at the LC interface does not prevent but greatly retards phospholipid adsorption relative to the protein-free interface of the LC (from <10 min to >90 min). Such retardation of the LC ordering transition by the presence of interfacial proteins was also seen when an aqueous-LC interface decorated with streptavidin was exposed to sodium dodecyl sulfate (SDS) (FIG. 4). Second, in contrast to the protein-free interface of the LC, for which the LC ordering transition was discontinuous and micrometer-sized domains of patterned LC were evident (FIG. 2a), the LC ordering transition in the presence of interfacial proteins was continuous. As discussed in more detail below, this continuous tilting of the LC orientation hints that the presence of the protein on the LC interface limits the size of the phospholipid domains to sub-optical sizes. Connected to this proposition, here we note also that the molecular-level mixing of phospholipids and proteins on the LC interface (no domains) would be expected to lead to a discontinuous transition in the orientation of the LC.[28,44]

Quantification of Proteins and Phospholipids at the Aqueous-5CB Interface.

To provide additional insight into the results described above, we quantified the interfacial density of phospholipid captured at the LC interface, along with the change in interfacial density of streptavidin at the LC interface following incubation against the dispersions of vesicles. Fluorescently-labeled vesicles (1 mol % BODIPY-DHPE) and proteins (1 mol % Texas Red-conjugated streptavidin) were used in these studies. The protein-decorated interface of the LC was imaged prior to and after exposure for 90 min to a dispersion of vesicles.

First, we sought to test our hypothesis that the accelerated ordering transition of 5CB triggered by specific binding of biotinylated vesicles to streptavidin adsorbed at the LC interface was the result of a biotin-mediated increase in local concentration of phospholipids near the interface. To this end, the epifluorescence intensity of BODIPY-DHPE was measured after the streptavidin-decorated aqueous-5CB interface was incubated against a dispersion of either biotinylated or non-biotinylated vesicles for 90 min and then flushed with TBS. Inspection of FIG. 5a reveals the BODIPY fluorescence at the LC interface that had been in contact with biotinylated vesicles to be substantially increased (see below for additional quantitative results). This result indicates that the specific binding event does lead to recruitment of additional phospholipids to the LC interfacial region relative to that observed in the absence of the specific binding interaction.

Figure 5:
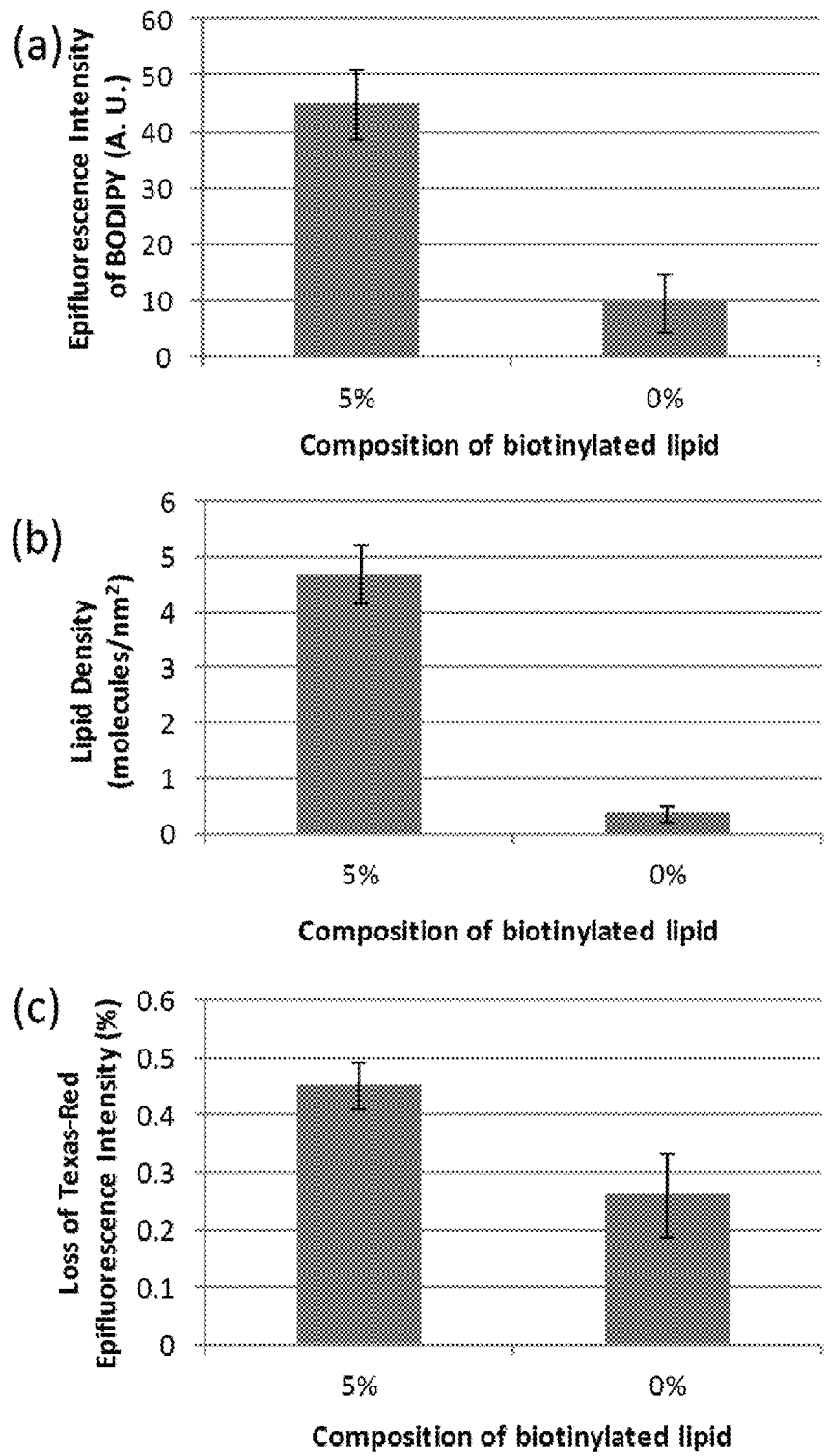
FIG. 5. Plot of (a) epifluorescence intensity of BODIPY-DHPE and (b) phospholipid density, both for a streptavidin-decorated aqueous-5CB interface following incubation against dispersions of vesicles with (5%) or without (0%) biotin-DOPE (50 µM of total phospholipid concentration, 1 mol % BODIPY-DHPE). (c) Plot of loss of epifluorescence intensity of Texas Red-conjugated streptavidin following incubation of a streptavidin-decorated interface of nematic 5CB (1 mol % labeled streptavidin) against dispersions of vesicles with (5%) or without (0%) biotin-DOPE.

By performing quantitative fluorimetric measurements of phospholipids extracted from the LC interface (see Methods), following incubation of the streptavidin-decorated LC interface against biotinylated vesicles, the density of interfacial phospholipid was determined to be $4.7 \pm 0.5$ molecules/nm$^2$ (FIG. 5b). We note that this density of lipid is greater than monolayer coverage, a point that we return to below.[10] A far smaller phospholipid density ($0.3 \pm 0.1$ molecules/nm$^2$) was measured for the interface that was incubated against biotin-free vesicles. These results are consistent with a physical picture in which specific binding of the biotinylated vesicles to streptavidin adsorbed at the LC interface leads to a higher local concentration of phospholipids, which, in turn, is transduced via the ordering transition of the LC.

We also investigated whether association of the phospholipid with the LC interface (and perturbation of the anchoring of 5CB) was accompanied by redistribution or displacement of the streptavidin from the interface. FIG. 5c shows that the density of streptavidin (as inferred by the fluorescence intensity of 1 mol % Texas Red-conjugated streptavidin at the interface) was measured to decrease at the LC interface that was incubated against biotin-free vesicles ($25 \pm 7\%$). The decrease was greater, however, when the vesicles were biotinylated ($46 \pm 4\%$). Since the decrease in interfacial density of streptavidin (FIG. 5c) coincides with an increase in interfacial concentration of phospholipid (FIGS. 5a and 5b), we interpret these results, when combined, to suggest that the displacement of streptavidin from the LC interface is driven by phospholipid adsorption. This interpretation is further supported by the observation that the streptavidin-decorated LC interface, when incubated against buffer free of vesicles for 90 min, exhibited negligible loss of Texas Red fluorescence.

Figure 6:
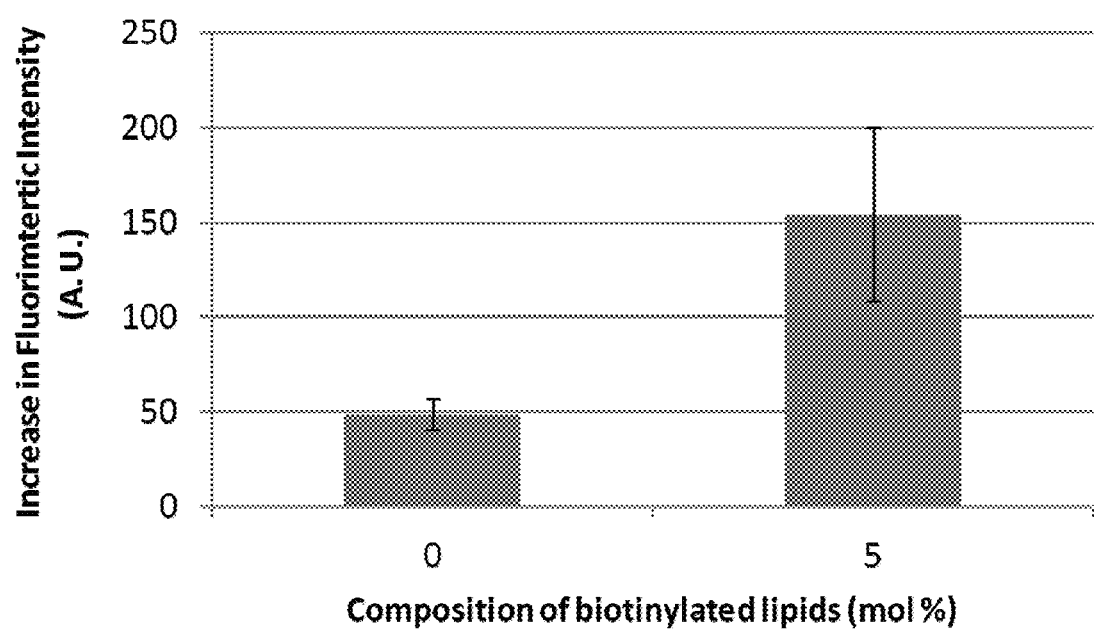
FIG. 6. Fluorimetric intensity of Texas Red-conjugated streptavidin in the solutions of vesicles which were incubated against the streptavidin-decorated aqueous-LC interface (1 mol % Texas Red-conjugated streptavidin). Fluorimetric measurements were performed with an excitation wavelength of 596 nm (0.5 nm excitation slit) and an emission wavelength range of 600-630 nm (5 nm emission slit) for the detection of Texas Red fluorescence. Control experiment using LC films that were not contacted with protein solution were performed to determine background fluorescence values.

Additionally, we conducted fluorimetric measurements using the bulk aqueous solutions against which the streptavidin-decorated interfaces of the LC had been incubated to assay for the presence of any Texas Red-conjugated streptavidin displaced from the interface into the bulk solution (FIG. 6). A higher Texas Red fluorescence intensity was measured in the dispersion of biotinylated vesicles as compared to the dispersion biotin-free vesicles ($154 \pm 45$ vs $48 \pm 8$ A.U.), providing further support for our conclusion that streptavidin was displaced by phospholipid adsorbing to the LC interface. We also note that the displacement of streptavidin from the interface is not complete (i.e., not all the fluorescence signals from the labeled streptavidin was lost). As discussed below, it is likely that that some streptavidin is bound to biotinylated lipid on the LC interface (via biotin-streptavidin binding) or co-exists along with phospholipid in an adsorbed state on the LC interface.[45]

Aging of Protein Adsorbed at the LC Interface.

As an additional test of the proposition that protein displacement from the LC interface is a necessary step in the above-described ordering transitions triggered by biotinylated vesicles, we investigated the effect of aging of the streptavidin on the LC interface on the LC ordering transition. Past studies have demonstrated that the interfacial shear viscosity of a protein film increases with age due to conformational changes and physical cross-linking of proteins on the interface.[46,47] In addition, adsorbed layers of proteins, when aged, have also been documented to produce interfacial elastic films that are displaced only by application of large external surface pressures.[48]

Figure 7:
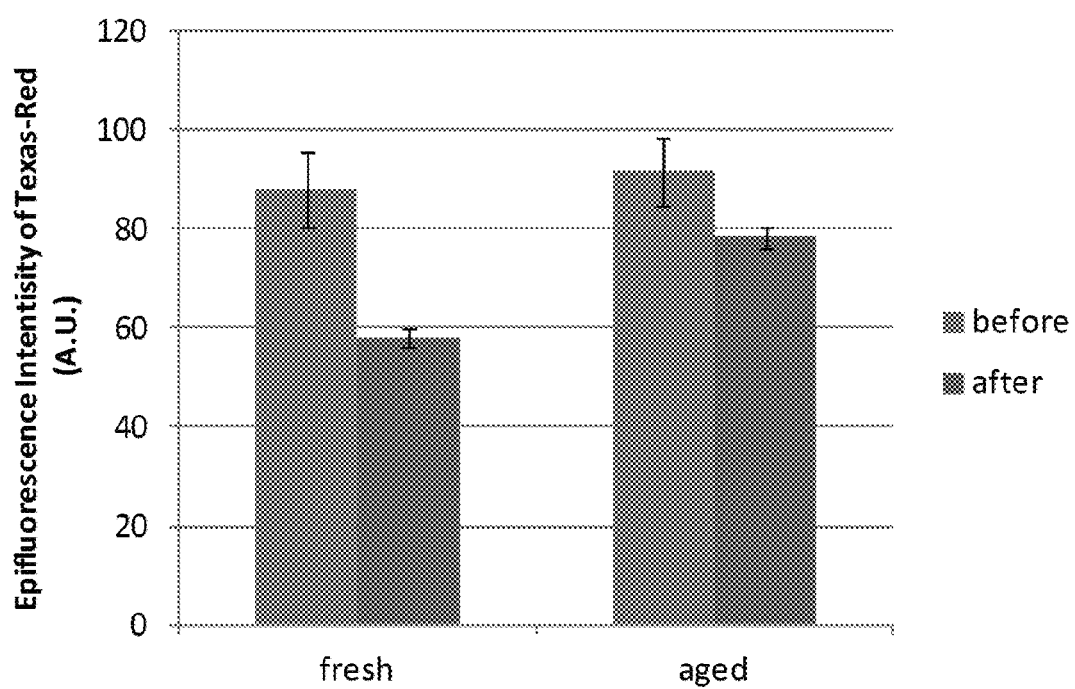
FIG. 7. Effect of protein aging on phospholipid-driven displacement of protein. Epifluorescence intensity of Texas Red-conjugated streptavidin at the aqueous-LC interface before and after incubated against dispersion of vesicles for 60 min, on both fresh and aged surfaces.

We hypothesized, therefore, that aging of the streptavidin would produce a state of the adsorbed protein that would be less readily displaced by phospholipid, resulting in a slower/retarded ordering transition of the LC. To test this hypothesis, we incubated the aqueous-5CB interface against a 1 µM solution of streptavidin for 90 min, rinsed the interface, and then left it overnight to "age" prior to exposure to a dispersion of vesicles (5 mol % biotin-DOPE). A control experiment conducted using Texas Red-conjugated streptavidin (1 mol %) verified that the fluorescence intensity of Texas Red at the LC interface remained constant after the overnight incubation, indicating negligible loss of streptavidin from the LC interface (FIG. 7).

Figure 8:
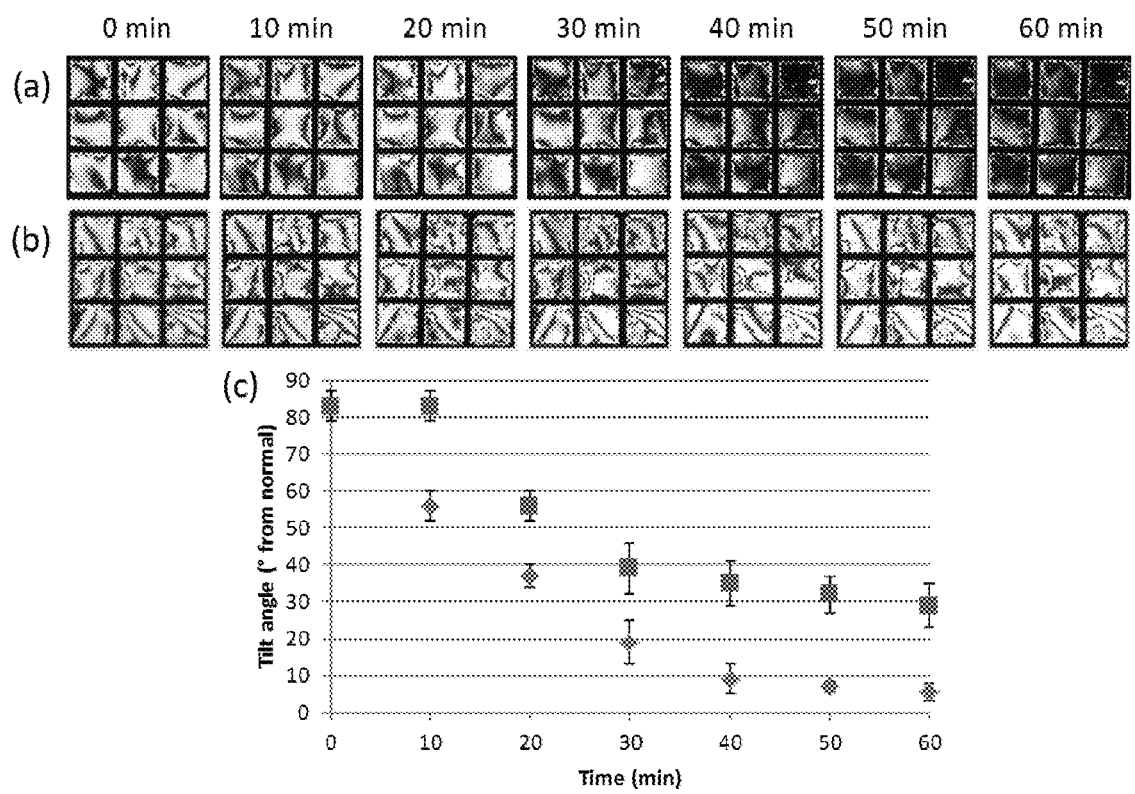
FIG. 8. Effect of protein aging on the LC ordering transition triggered by specific binding of biotinylated vesicles to a protein-decorated interface of a LC. (a) Optical images (crossed polarizers) of nematic 5CB upon incubation of a freshly-prepared streptavidin-decorated aqueous-LC interface against biotinylated vesicles (0.1 mM). In (b), the streptavidin-decorated interface was aged overnight prior to incubation against biotinylated vesicles. (c) Tilt angle of 5CB at the aqueous-LC interfaces corresponding to (a) diamonds and (b) squares.

A comparison of FIGS. 8a and 8b reveals that the LC ordering transition triggered by specific binding of biotinylated vesicles was, indeed, retarded by aging of the interfacial streptavidin. Epifluorescence measurements also showed that the decrease in signal from Texas Red-conjugated streptavidin at the aged interface (following incubation against the biotinylated vesicles for 60 min) ($15 \pm 2\%$) was less than that observed at the streptavidin-decorated interface that was not aged ($34 \pm 2\%$) (FIG. 7). These results thus provide support for our conclusion that the LC ordering transition induced by specific binding of biotinylated vesicles involves displacement of streptavidin from the LC interface, and that an aged protein layer at the aqueous-5CB interface slows the displacement process when exposed to phospholipid (FIG. 3c). As noted above, a number of past studies have concluded that aged protein films become increasingly difficult to displace from interfaces using amphiphiles.[47,49]

Effect of Interfacial Density of Streptavidin.

Next, we examined how the density of streptavidin adsorbed onto the aqueous-5CB interface influenced the LC ordering transitions induced by binding of biotinylated vesicles. Based on the hypothesis described above, we predicted that an increase in the interfacial density of streptavidin would inhibit incorporation of the phospholipids onto the LC interface, and thus slow the LC ordering transition. Inspection of FIG. 9, however, reveals that the LC ordering transition induced by specific binding of the biotinylated vesicles was accelerated with increasing interfacial density of streptavidin (FIG. 9a-d). This result is, at first sight, seemingly contradictory of the above-described hypothesis. The trend seen in FIG. 9a-d was also seen when the LC interface was exposed to biotin-free vesicles. That is, streptavidin adsorbed to the LC interface from a solution of high streptavidin concentration gave rise to a fast ordering transition when the interface was incubated against non-biotinylated vesicles (FIG. 10).

We note, however, that past studies have also demonstrated that crowding of proteins within an adsorbed layer (leading to lateral, steric interactions) can impact the conformational state of the protein at the interface. That is, when the interfacial density of protein at an interface is high, space available for the protein to spread and unfold at the surface is low.[50,51] As mentioned above, unfolding of proteins permits intermolecular interactions between neighboring proteins, as well as stronger adsorption of proteins to the interface.[50] Thus, we interpret the results described above to suggest that the ordering transition of 5CB induced by binding of vesicles to the LC interface is accelerated at high interfacial densities of streptavidin due to either weaker inter-protein associations and/or weaker adsorption of the proteins onto to the LC interface, both of which permits facile displacement of proteins from the interface by phospholipids (FIGS. 3b and 3c). This interpretation is consistent also with the above-noted effects of aging of the proteins on the LC interface.

Figure 9:
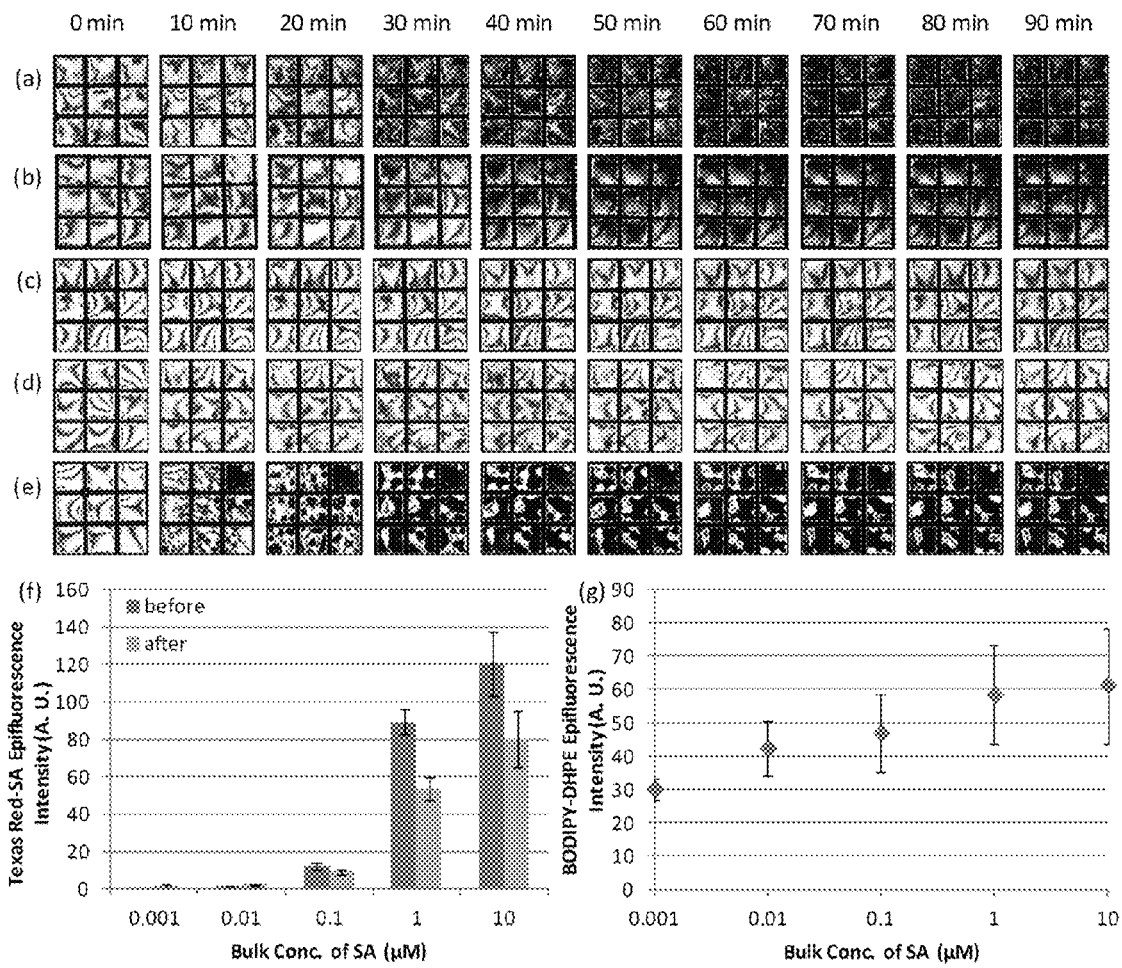
FIG. 9. Influence of the interfacial density of streptavidin on ordering transitions induced in nematic 5CB by specific binding of biotinylated vesicles. (a-e) Optical images (crossed polarizers) of nematic 5CB upon incubation of streptavidin-decorated aqueous-LC interfaces against biotinylated vesicles (0.1 mM, 5 mol % biotin-DOPE). The interfaces were contacted with solutions of streptavidin having concentrations of (a) 10, (b) 1, (c) 0.1, (d) 0.01, and (e) 0.001 µM prior to incubation against the dispersions of biotinylated vesicles. (f) Plot of epifluorescence intensity of Texas Red-conjugated streptavidin (1 mol %) before and after incubation of the LC interfaces against the dispersions of biotinylated vesicles. (g) Plot of the increase in epifluorescence intensity of BODIPY-DHPE upon incubation of streptavidin-decorated LC interfaces against dispersions of vesicles (1 mol % BODIPY-DHPE).

In support of the above-described interpretation, FIG. 9f shows the change in fluorescence intensity of Texas Red-conjugated streptavidin at the LC interface following incubation against dispersions of biotinylated vesicles, as a function of the interfacial density of streptavidin. This data reveals that the loss of streptavidin from the LC interface (inferred from the decrease in Texas Red fluorescence intensity) is indeed more pronounced at the higher initial interfacial densities of streptavidin. We also note that the amount of streptavidin adsorbed onto the LC interface from solutions containing intermediate bulk concentrations is low (e.g., for 0.1 µM in FIG. 9f, we estimate the coverage of protein to be ~10% of saturation coverage). Interestingly, the presence of this low interfacial concentration of protein is sufficient to retard the ordering transition of the LC upon incubation against dispersions of biotinylated vesicles (FIG. 9c). As noted above, we infer that the state of the bound protein (strongly bound and likely partially unfolded) hinders adsorption of phospholipids onto the LC interface at the low coverage evident in FIG. 9 (see also FIG. 3c).

Figure 11:
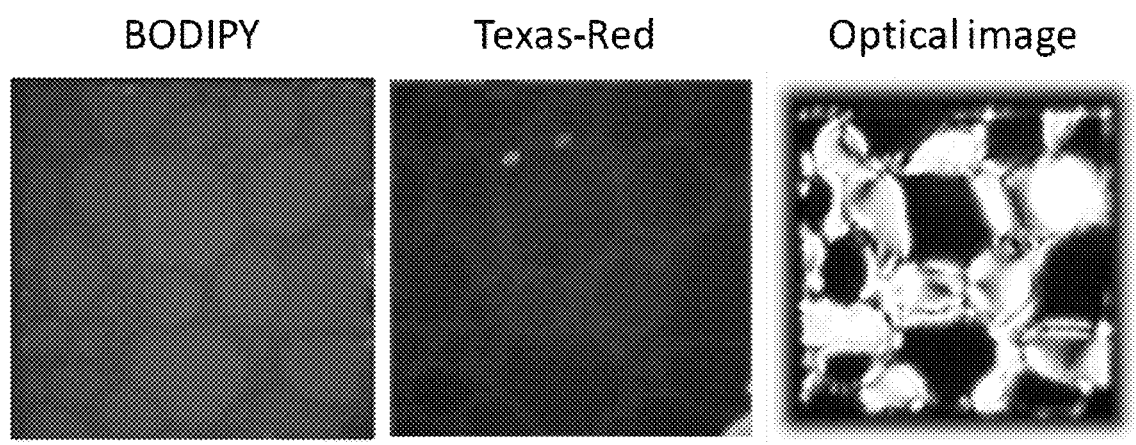
FIG. 11: Respective epifluorescence (enhanced contrast) and optical images for a streptavidin-decorated aqueous-LC interface that was incubated with 0.001 µM of streptavidin and subsequently exposed to lipid vesicles (0.1 mM).

When the density of streptavidin adsorbed to the LC interface was less than a few percent of saturation coverage (prepared from a solution of 0.001 µM), we observed incubation of the LC interface against biotinylated vesicles to cause the nucleation and growth of homeotropic regions of LC (not a continuous change in the tilt of the LC) (FIG. 9e). For these interfaces, by using epifluorescence imaging, we observed the lateral segregation of streptavidin (1 mol % Texas Red-conjugated) (FIG. 11). Specifically, we established that the homeotropic domains of LC corresponded to lipid-rich regions (appears bright when imaged for BODIPY-DHPE) and the co-existing planar LC domains corresponded to protein-rich regions of the interface. This result suggests that at sufficiently low concentrations of streptavidin, lateral reorganization of phospholipid and protein on the interface leads to lipid- and protein-rich domains on micrometer and larger scales (FIG. 11).

Finally, we quantified the amount of phospholipid captured at the LC interface as a function of interfacial density of streptavidin. FIG. 9g indicates that the amount of phospholipid captured at the interface increases with density of interfacial streptavidin, such that the LC interface with the highest density of streptavidin captures roughly twice the amount of phospholipid captured at the LC interface with the lowest density of streptavidin. Since a phospholipid density of $4.7 \pm 0.5$ molecules/nm$^2$ was measured at the LC interface that had been incubated with 1 µM of streptavidin, we conclude that the amount of phospholipid captured in the interfacial region under all conditions exceeds monolayer coverage (~2 molecules/nm$^2$) and thus is sufficient, in principle, to trigger homeotropic ordering of the LC if adsorbed onto the LC interface.[10] The slow LC response at intermediate densities of streptavidin (0.1 and 0.01 µM, FIGS. 9c and 9d) is, therefore, not due to insufficient phospholipid in the interfacial region. We conclude that it is likely that the phospholipid exists at the LC interface in at least two states.[45]

One state of the phospholipid interacts with the LC, and thus contributes to the observed ordering of the LC. A second population of phospholipid, while bound to the interfacial region, likely does not interact directly with the LCs but is bound to the streptavidin at the LC interface (e.g., adsorbed vesicles). This proposition is supported by our measurement of the presence of lipids (indicated by BODIPY fluorescence) in regions of the LC interface that exhibit planar LC orientations (FIG. 11).

Ordering Transitions at Interfaces of 5CB Decorated with Anti-biotin Antibody.

Figure 12:
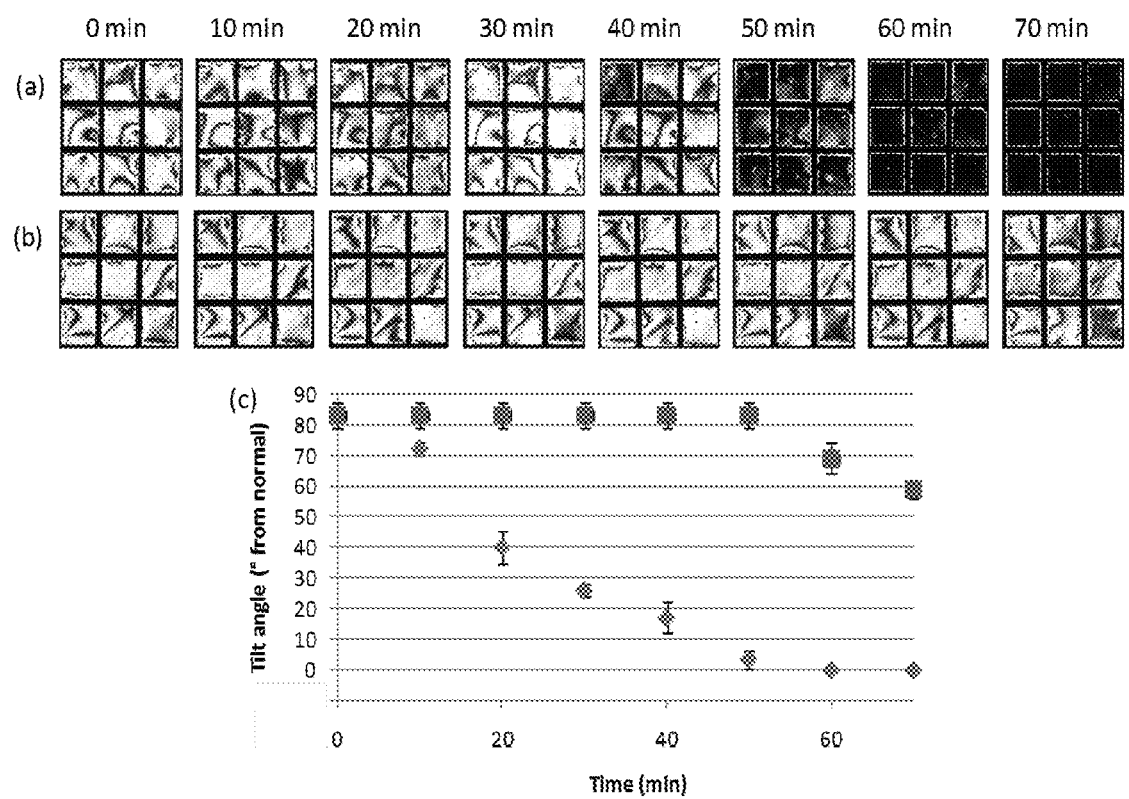
FIG. 12. Ordering transitions induced in films of nematic 5CB by specific binding of biotinylated vesicles (0.1 mM) to anti-biotin antibody-decorated aqueous-5CB interfaces. Optical images (crossed polarizers) of nematic 5CB that result from incubation of anti-biotin antibody-decorated interface against dispersions of vesicles containing (a) 5 mol % and (b) 0 mol % biotin-DOPE. (c) Tilt angle of 5CB at the aqueous-LC interfaces corresponding to (a) diamonds and (b) squares.

We end this example by reporting that the interfacial phenomena described above using biotin and streptavidin are also seen when the LC is decorated with proteins other than streptavidin. Specifically, we prepared an anti-biotin antibody-decorated interface of 5CB by incubating an aqueous-LC interface against a buffered solution containing 0.05 mg/ml of the antibody. FIG. 12 shows that, similar to a streptavidin-decorated LC interface, an accelerated ordering transition of LC was observed when the anti-biotin antibody-decorated LC interface was incubated against a dispersion of biotinylated vesicles (relative to a control experiment using biotin-free vesicles).

Figure 13:
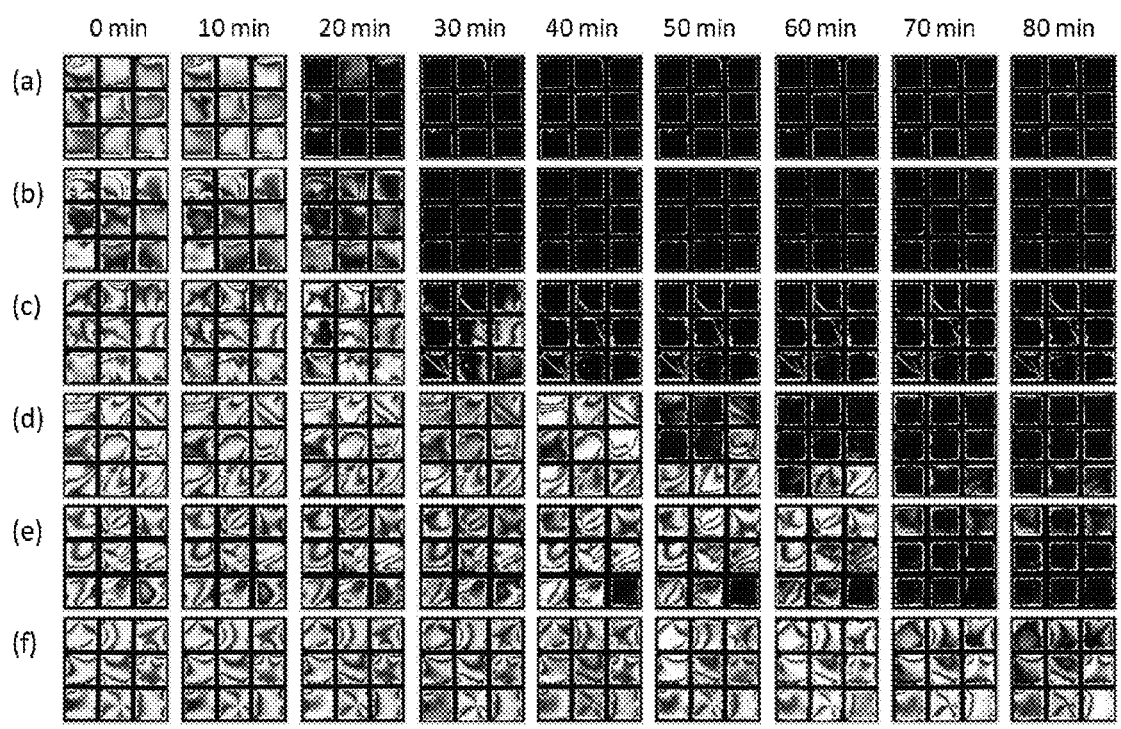
FIG. 13. Interaction of biotinylated vesicles with aqueous-5CB interfaces of varying interfacial density of anti-biotin antibody. Optical images (crossed polarizers) of 5CB after incubation of anti-biotin antibody-decorated LC interface against dispersions of vesicles (0.1 mM, 5 mol % biotin-DOPE). The interfaces were in contact with a solution of anti-biotin antibody at bulk concentrations of (a) 1.3, (b) 0.3, (c) 0.17, (d) 0.04, (e) 0.02, and (f) 0.01 µM.

The LC ordering transition also occurred via a continuous change in the tilt of the LC. When the interfacial density of the anti-biotin antibody at the LC interface was decreased (by decreasing the concentration of the antibody within the bulk aqueous solution against which the LC interface was incubated), the ordering transition induced by binding of biotinylated vesicles was retarded (FIG. 13), similar to the result shown in FIG. 9 with the streptavidin-decorated LC interfaces. Overall, this experiment illustrates that ordering transitions in LCs can be induced by specific binding of vesicles via antibody-antigen interactions. We conclude that the interfacial phenomena reported in this manuscript are potentially generalizable to a range of other receptor-ligand interactions involving vesicles.

Discussion.

One of the key findings of the study reported in this example is that the antagonistic influence of adsorbed proteins and phospholipids on the orientational ordering of LCs can, under some circumstances, give rise to continuous ordering transitions in LCs. As mentioned above, a number of past studies have established that the hydrocarbon tails of phospholipids play a dominant role in dictating the homeotropic orientation of LCs at lipid-laden LC interfaces.[9,10] In particular, early studies concluded that lipid tail length and areal density are important determinants of the ordering of LCs by lipids.[52] Unlike phospholipids, most proteins do not possess long alkyl tails and therefore do not cause homeotropic alignment of LCs. Indeed, while elucidation of the intermolecular interactions responsible for anchoring of LCs on protein and peptide-decorated interfaces is an ongoing area of research,[53] most protein-functionalized surfaces give rise to planar anchoring of LCs.[25-27]

The continuous nature of the LC ordering transitions induced by binding of vesicles to protein-decorated LC interfaces, as reported in this example, is significant in light of several previous studies. Specifically, Brake and co-workers showed that when a monolayer of phospholipid (containing 2 mol % biotinylated lipid) was formed at an aqueous-LC interface by fusion of vesicles and subsequently exposed to a solution of neutravidin, micrometer-scale domains comprised of segregated proteins and lipids were observed at the LC interface.[9] This segregation of species led to patterned orientations of the LC. Furthermore, de Tercero et al. demonstrated that non-specific interactions of proteins with interfaces of 5CB decorated with partial monolayers of DLPC also led to formation of micrometer-sized, patterned domains of LC, consistent with penetration of the protein into the lipid-laden interface (and segregation of the species at the interface).[54]

In contrast to these past studies, the interaction of vesicles with protein-decorated LC interfaces, as reported in this example, does not lead to micrometer-scale, lateral segregation of phospholipids and proteins leading to domains of either planar or homeotropic ordering of LCs. Instead, the continuous tilting of the LC reported in this paper suggests a physical picture where phospholipids and proteins form sub-optical domains (see below).

The above-described interpretation of the continuous ordering transition is inspired by previous studies that have reported that heterogeneous interfaces comprised of nanoscopic patches that cause homeotropic or planar anchoring of LCs can give rise to micrometer-scale tilting of the LC.[28,55] The pattern of local surface-imposed orientations of the LC becomes homogeneous in the bulk of the LC in order to minimize the elastic energy of the LC (by relaxing the discontinuity in the director field near the alignment layer). In contrast, a mixture of two species, one of which causes homeotropic alignment and the other causes planar alignment, if mixed homogeneously at the molecular level, will not give rise to tilted states of the LC. That is, for a molecularly mixed alignment layer, the change from planar to homeotropic alignment (or vice versa) occurs in a discontinuous manner.[28,44] The observation of a continuous change in the tilt of the LC is, therefore, consistent with an inhomogeneous LC interface comprised of nano-domains of proteins and phospholipids.

Another significant observation reported in this example is the dependence of the response of the LC on the state of the proteins adsorbed onto the LC interface. Many past studies have reported that proteins undergo conformational changes upon adsorption to interfaces.[56] For example, at hydrophobic interfaces, proteins expose their hydrophobic (interior) amino acid residues to maximize interactions of these residues with the hydrophobic interfaces. This restructuring (denaturation) of the protein can promote cross-linking of proteins on the interface and the formation of a cohesive gel-network.[57] Of particular relevance to our studies, Mackie and co-workers have shown that surfactant-driven displacement of a protein film becomes increasingly difficult with increasing age of the protein film.[47]

The extent of conformational change of the proteins is also affected by the degree of crowding of proteins at interfaces: The lower the interfacial density of proteins, the more space proteins have to spread and unfold to maximize their interactions with the interface.[50] For example, Norde and co-workers have demonstrated that the α-helix content of serum albumin decreases with decreasing surface coverage.[51] Our observation that LC ordering transitions induced by specific capture of vesicles are influenced by both aging and crowding of proteins at the interface suggests that the conformational state of the proteins at the LC interface is a central factor underlying these LC ordering transitions.

We interpret our results to suggest that the LC ordering transitions involve at least two key processes. The first process involves the accumulation of phospholipid near the interfacial region of the LC via specific binding of the vesicles to the protein-decorated interface. The second process is the phospholipid-driven displacement of the proteins from the LC interface. Protein films that are difficult to displace impede incorporation of lipids into the interface of the LC.[47]

Finally, we note that several studies have reported that biomolecular interactions (enzymatic events[58], hybridization of DNA[3], antibody-antigen interaction[59]) can perturb the ordering of LCs at amphiphile-decorated interfaces. While the molecular mechanisms underlying several of the ordering transitions remain to be fully elucidated, these past examples, when combined with the current study, serve to illustrate the richness of interfacial phenomena that result from the competing influences of proteins and amphiphiles on the ordering of LCs at LC-aqueous interfaces.

CONCLUSION

A key conclusion of the study reported in this example is that interfaces between LCs and aqueous solutions, when decorated with proteins, permit specific binding events involving vesicles to be amplified into orientational transitions in the LC. We interpret our results to indicate that the ordering transition reflects the competitive interactions of interfacial proteins and phospholipids with the LCs. Accumulation of vesicles at the LC interface due to specific binding of ligands with receptors pre-adsorbed at the interface facilitates the transfer of phospholipids from the vesicles to the interface of LC, which in turn triggers a continuous ordering transition of the LC to a homeotropic orientation and a distinct change in the optical appearance of the LC.

Non-specific interactions of vesicles with protein-decorated LC interfaces were also observed to cause ordering transitions in the LC, but the dynamics of those transitions were significantly slower than that observed in the presence of the specific binding events. Significantly, the response of the streptavidin-decorated LC to vesicle binding was a continuous change in the tilt of the LC, hinting at the likely presence of sub-micrometer domains of proteins and phospholipids.

Our results also reveal that the LC ordering transition is influenced by aging and crowding of the interfacial proteins. Both effects are consistent with the proposition that the state of the proteins adsorbed onto the LC interface influences the ease of displacement of the proteins from the interface by phospholipids, a process that appears to be necessary for the LC ordering transition to be observed. Finally, the phenomena reported in this paper using the streptavidin-biotin system were observed also when using a LC interface decorated with anti-biotin antibody.

Overall, the results presented in this example suggest that LCs offer the basis of a novel tool for fundamental studies of proteins and amphiphiles at interfaces and, specifically, they offer new methods to report for specific capture of ligand-containing vesicles on protein-decorated interfaces.

The invention is not limited to the embodiments set forth herein for illustration, but includes everything that is within the scope of the claims. Furthermore, all references cited herein are hereby incorporated by reference in their entirety and for all purposes as if fully set forth herein.

CITED REFERENCES (1) Lockwood, N. A.; Abbott, N. L. *Current Opinion in Colloid & Interface Science* 2005, 10, 111-120.
(2) Lockwood, N. A.; Gupta, J. K.; Abbott, N. L. *Surface Science Reports* 2008, 63, 255-293.
(3) Price, A. D.; Schwartz, D. K. *Journal of the American Chemical Society* 2008, 130, 8188-8194.
(4) Kinsinger, M. I.; Sun, B.; Abbott, N. L.; Lynn, D. M. *Advanced Materials* 2007, 19, 4208-4212.
(5) Lee, D. Y.; Seo, J. M.; Khan, W.; Komfield, J. A.; Kurji, Z.; Park, S. Y. *Soft Matter* 2010, 6, 1964-1970.
(6) Jerome, B. *Reports on Progress in Physics* 1991, 54, 391-451.
(7) de Gennes, P. G.; Prost, J. *The Physics of Liquid Crystals*; Oxford University, London, 1994.
(8) Collings, P. J.; Hird, M. *Introduction to Liquid Crystals Chemistry and Physics*; Taylor & Francis: London, 1997.
(9) Brake, J. M.; Daschner, M. K.; Luk, Y. Y.; Abbott, N. L. *Science* 2003, 302, 2094-2097.
(10) Meli, M. V.; Lin, I. H.; Abbott, N. L. *Journal of the American Chemical Society* 2008, 130, 4326-4333.
(11) Brake, J. M.; Daschner, M. K.; Abbott, N. L. *Langmuir* 2005, 21, 2218-2228.
(12) Brake, J. M.; Mezera, A. D.; Abbott, N. L. *Langmuir* 2003, 19, 6436-6442.
(13) Lockwood, N. A.; de Pablo, J. J.; Abbott, N. L. *Langmuir* 2005, 21, 6805-6814.
(14) Fletcher, P. D. I.; Kang, N. G.; Paunov, V. N. *ChemPhysChem* 2009, 10, 3046-3053.
(15) Gupta, J. K.; Meli, M. V.; Teren, S.; Abbott, N. L. *Physical Review Letters* 2008, 100, 48301.
(16) Gupta, J. K.; Abbott, N. L. *Langmuir* 2009, 25, 2026-2033.
(17) Kinsinger, M. I.; Lynn, D. M.; Abbott, N. L. *Soft Matter* 2010, 6, 4095-4104.
(18) Tan, L. N.; Bertics, P. J.; Abbott, N. L. *Langmuir* 2011, 27, 1419-1429.
(19) Stora, T.; Dienes, Z.; Vogel, H.; Duschl, C. *Langmuir* 2000, 16, 5471-5478.
(20) Pignataro, B.; Steinem, C.; Galla, H. J.; Fuchs, H.; Janshoff, A. *Biophysical Journal* 2000, 78, 487-498.
(21) Berquand, A.; Mazeran, P. E.; Pantigny, J.; Proux-Delrouyre, V.; Laval, J. M.; Bourdillon, C. *Langmuir* 2003, 19, 1700-1707.
(22) Städler, B.; Falconnet, D.; Pfeiffer, I.; Höök, F.; Vörös, J. *Langmuir* 2004, 20, 11348-11354.
(23) Brake, J. M.; Abbott, N. L. *Langmuir* 2002, 18, 6101-6109.
(24) Brake, J. M.; Abbott, N. L. *Langmuir* 2007, 23, 8497-8507.
(25) Tingey, M. L.; Wilyana, S.; Snodgrass, E. J.; Abbott, N. L. *Langmuir* 2004, 20, 6818-6826.
(26) Jang, C. H.; Tingey, M. L.; Korpi, N. L.; Wiepz, G. J.; Schiller, J. H.; Bertics, P. J.; Abbott, N. L. *Journal of the American Chemical Society* 2005, 127, 8912-8913.
(27) Luk, Y. Y.; Tingey, M. L.; Hall, D. J.; Israel, B. A.; Murphy, C. J.; Bertics, P. J.; Abbott, N. L. *Langmuir* 2003, 19, 1671-1680.
(28) Kwok, H. S.; Li, Y. W.; Yeung, F. S. *Molecular Crystals and Liquid Crystals* 2009, 507, 26-40.
(29) Al-Nedawi, K.; Meehan, B.; Rak, J. *Cell Cycle* 2009, 8, 2014-2018.
(30) Muralidharan-Chari, V.; Clancy, J. W.; Sedgwick, A.; D'Souza-Schorey, C. *Journal of Cell Science* 2010, 123, 1603.
(31) Drzaic, P. S. *Liquid Crystal Dispersions*; World Scientific Singapore, 1995; Vol. 1.
(32) Bloss, F. D. *An Introduction to the Methods of Optical Crystallography*; Holt, Rinehart and Winston: New York, 1961.
(33) Brake, J. M.; Mezera, A. D.; Abbott, N. L. *Langmuir* 2003, 19, 8629-8637.
(34) Chigrinov, V. G. *Electrooptic Effects in Liquid Crystal Materials*; Springer Verlag: New York, 1993.
(35) Lin, I. H.; Meli, M. V.; Abbott, N. L. *Journal of Colloid and Interface Science* 2009, 336, 90-99.
(36) Graham, D. E.; Phillips, M. C. *Journal of Colloid and Interface Science* 1979, 70, 427-439.
(37) Beverung, C. J.; Radke, C. J.; Blanch, H. W. *Biophysical chemistry* 1999, 81, 59-80.
(38) Mackie, A. R.; Gunning, A. P.; Wilde, P. J.; Morris, V. J. *Langmuir* 2000, 16, 2242-2247.
(39) Lockwood, N. A.; Mohr, J. C.; Ji, L.; Murphy, C. J.; Palecek, S. P.; de Pablo, J. J.; Abbott, N. L. *Advanced Functional Materials* 2006, 16, 618-624.
(40) Chao, C. Y.; Carvajal, D.; Szleifer, I.; Shull, K. R. *Langmuir* 2008, 24, 2472-2478.
(41) Green, N. M. *Methods in enzymology* 1990, 184, 51.
(42) Tjipto, E.; Cadwell, K. D.; Quinn, J. F.; Johnston, A. P. R.; Abbott, N. L.; Caruso, F. *Nano letters* 2006, 6, 2243-2248.
(43) Sonin, A. A. *Freely Suspended Liquid Crystalline Films*, John Wiley & Sons: New York, 1998.
(44) Zhang, K.; Liu, N.; Twieg, R.; Auman, B.; Bos, P. *Liquid Crystals* 2008, 35, 1191-1197.
(45) Waninge, R.; Walstra, P.; Bastiaans, J.; Nieuwenhuijse, H.; Nylander, T.; Paulsson, M.; Bergenstahl, B. *Journal of Agricultural and Food Chemistry* 2005, 53, 716-724.
(46) Roth, S.; Murray, B. S.; Dickinson, E. *Journal of Agricultural and Food Chemistry* 2000, 48, 1491-1497.
(47) Mackie, A. R.; Gunning, A. P.; Pugnaloni, L. A.; Dickinson, E.; Wilde, P. J.; Morris, V. J. *Langmuir* 2003, 19, 6032-6038.
(48) Freer, E. M.; Yim, K. S.; Fuller, G. G.; Radke, C. J. *The Journal of Physical Chemistry B* 2004, 108, 3835-3844.
(49) Patino, J. M. R.; Nino, M. R. R.; Sanchez, C. C. *Current Opinion in Colloid & Interface Science* 2003, 8, 387-395.
(50) Dickinson, E. *Colloids and Surfaces B: Biointerfaces* 1999, 15, 161-176.
(51) Norde, W.; Favier, J. P. *Colloids and surfaces* 1992, 64, 87-93.
(52) Hiltrop, K.; Stegemeyer, H. *Berichte Der Bunsen-Gesellschaft-Physical Chemistry Chemical Physics* 1981, 85, 582-588.
(53) Bai, Y.; Abbott, N. L. *Journal of the American Chemical Society*.
(54) De Tercero, M. D.; Abbott, N. L. *Chemical Engineering Communications* 2008, 196, 234-251.

(55) Yeung, F. S.; Ho, J. Y.; Li, Y. W.; Xie, F. C.; Tsui, O. K.; Sheng, P.; Kwok, H. S. *Applied physics letters* 2006, 88, 051910.

(56) Roach, P.; Farrar, D.; Perry, C. C. *Journal of the American Chemical Society* 2005, 127, 8168-8173.

(57) Freer, E. M.; Yim, K. S.; Fuller, G. G.; Radke, C. J. *Langmuir* 2004, 20, 10159-10167.

(58) Park, J. S.; Abbott, N. L. *Advanced Materials* 2008, 20, 1185-1190.

(59) Alino, V. J. R.; Pang, J.; Yang, K. L. *Langmuir* 2011, 27, 11784-11789.

We claim:

1. A method for assaying the effectiveness of a putative protein stabilizing agent, the method comprising:
   (a) providing one or more proteins and a putative protein stabilizing agent at an interface between an aqueous phase and a nematic liquid crystal phase;
   (b) aging the interface and associated proteins;
   (c) contacting the interface with a composition comprising a ligand-functionalized phospholipid vesicle, wherein the ligand is capable of binding to the one or more proteins; and
   (d) observing the orientational ordering of the nematic liquid crystal at the interface;
   wherein the rate of change in the orientational ordering, the extent of change in the orientational ordering, or both, is correlated with the effectiveness of the putative protein stabilizing agent.

2. The method of claim 1, wherein the ligand is biotin.

3. The method of claim 1, wherein the one or more proteins are selected from the group consisting of streptavidin, conjugated streptavidin, and anti-biotin antibody.

4. The method of claim 1, wherein the step of observing the orientational ordering of the nematic liquid crystal at the surface comprises calculating the tilt angle of the nematic liquid crystal at the interface relative to the interface normal, wherein the tilt angle indicates the extent of the change in orientational ordering.

5. The method of claim 4, wherein the tilt angle is calculated from the effective birefringence of the nematic liquid crystal under light illumination.

6. The method of claim 1, wherein the nematic liquid crystal is 4-pentyl-4'-cyanobiphenyl (5CB).

7. A method for assaying the optimal concentration of a protein for preventing the unfolding of the protein, the method comprising:
   (a) providing one or more proteins at a known concentration at an interface between an aqueous phase and a nematic liquid crystal phase;
   (b) aging the interface and associated proteins;
   (c) contacting the interface with a composition comprising a ligand-functionalized phospholipid vesicle, wherein the ligand is capable of binding to the one or more proteins; and
   (d) observing the orientational ordering of the nematic liquid crystal at the interface;
   wherein the rate of change in the orientational ordering, the extent of change in the orientational ordering, or both, is correlated with the effectiveness of the known concentration for preventing the unfolding of the protein.

8. The method of claim 7, wherein the ligand is biotin.

9. The method of claim 8, wherein the one or more proteins are selected from the group consisting of streptavidin, conjugated streptavidin, and anti-biotin antibody.

10. The method of claim 7, wherein the step of observing the orientational ordering of the nematic liquid crystal at the surface comprises calculating the tilt angle of the liquid crystal at the interface relative to the interface normal, wherein the tilt angle indicates the extent of the change in orientational ordering.

11. The method of claim 10, wherein the tilt angle is calculated from the effective birefringence of the liquid crystal under light illumination.

12. The method of claim 7, wherein the nematic liquid crystal is 4-pentyl-4'-cyanobiphenyl (5CB).

13. A device for assaying the effectiveness of a putative protein stabilizing agent, the device comprising an interface between an aqueous phase and a nematic liquid crystal phase, said interface comprising one or more proteins and further comprising a composition comprising a ligand-functionalized phospholipid vesicle, wherein the ligand is capable of binding to the one or more proteins, and a putative protein stabilizing agent;
   wherein the nematic liquid crystal at the interface exhibits a continuous orientation ordering tilt angle relative to the interface normal that is intermediate between planar (parallel to the interface) and homeotropic (perpendicular to the interface).

14. The device of claim 13, wherein the ligand is biotin.

15. The device of claim 13, wherein the one or more proteins are selected from the group consisting of streptavidin, conjugated streptavidin, and anti-biotin antibody.

16. The device of claim 13, wherein the tilt angle is between 10° and 80° relative to the interface normal.

17. The device of claim 16, wherein the tilt angle is between 30° and 60° relative to the interface normal.

18. The device of claim 13, wherein the nematic liquid crystal is 4-pentyl-4'-cyanobiphenyl (5CB).

* * * * *